(12) United States Patent
Lin et al.

(10) Patent No.: US 8,682,416 B2
(45) Date of Patent: Mar. 25, 2014

(54) ROBOTIC MODULE FOR NATURAL ORIFICE TRANSLUMINAL ENDOSCOPIC SURGERY (NOTES)

(75) Inventors: Ching-Fang Lin, Simi Valley, CA (US); Stephen Oonk, Simi Valley, CA (US)

(73) Assignee: American GNC Corporation, Simi Valley, CA (US)

( * ) Notice: Subject to any disclaimer, the term of this patent is extended or adjusted under 35 U.S.C. 154(b) by 240 days.

(21) Appl. No.: 13/135,544

(22) Filed: Jul. 8, 2011

(65) Prior Publication Data

US 2013/0012821 A1    Jan. 10, 2013

(51) Int. Cl.
*A61B 19/00* (2006.01)
*A61B 6/00* (2006.01)

(52) U.S. Cl.
USPC .......................................... 600/473; 606/130

(58) Field of Classification Search
None
See application file for complete search history.

(56) References Cited

U.S. PATENT DOCUMENTS

2009/0171373 A1* 7/2009 Farritor et al. ................ 606/130
2012/0179168 A1* 7/2012 Farritor et al. ................ 606/130

* cited by examiner

*Primary Examiner* — Bill Thomson
*Assistant Examiner* — Scott T Luan
(74) *Attorney, Agent, or Firm* — Raymond Y. Chan; David and Raymond Patent Firm

(57) ABSTRACT

A miniature in-vivo robotic module to be used for conducting dexterous manipulations on organs and other target entities in a patient's abdominal or peritoneal cavity as part of Natural Orifice Transluminal Endoscopic Surgery (NOTES) is disclosed in this invention. The robotic module is a serial manipulator consisting of seven cylindrical links and six actively controllable rotational degrees of freedom, thereby enabling an end effector equipped with a laparoscopic type instrument to assume a commanded position and orientation within the robot's workspace. After overtube navigation starting from a natural orifice or preexisting wound, the module must be anchored and guided to a designated location along the inner abdominal cavity wall. This is accomplished via magnetic coupling forces between internal embedded magnets and magnets fixed to the end of a different robotic manipulator located external to the patient.

17 Claims, 37 Drawing Sheets

| Link $i=$ | $a_i$ | $d_i$ | $\alpha_i$ | $\theta_i$ |
|---|---|---|---|---|
| 1 | $l_1$ | 0 | 90° | $\theta_1$ |
| 2 | $l_2$ | 0 | 0 | $\theta_2$ |
| 3 | $l_3$ | 0 | 0 | $\theta_3$ |
| 4 | $l_4$ | 0 | -90° | $\theta_4$ |
| 5 | 0 | 0 | 90° | 90° + $\theta_5$ |
| 6 | 0 | $l_5 + l_6$ | 0 | $\theta_6$ |

$$A_{i-1}^{i} = \begin{bmatrix} \cos\theta_i & -\cos\alpha_i \sin\theta_i & \sin\alpha_i \sin\theta_i & a_i \cos\theta_i \\ \sin\theta_i & \cos\alpha_i \cos\theta_i & -\sin\alpha_i \cos\theta_i & a_i \sin\theta_i \\ 0 & \sin\alpha_i & \cos\alpha_i & d_i \\ 0 & 0 & 0 & 1 \end{bmatrix}$$

$$A_0^1 = \begin{bmatrix} \cos\theta_1 & 0 & \sin\theta_1 & l_1 \cos\theta_1 \\ \sin\theta_1 & 0 & -\cos\theta_1 & l_1 \sin\theta_1 \\ 0 & 1 & 0 & 0 \\ 0 & 0 & 0 & 1 \end{bmatrix}
\quad
A_1^2 = \begin{bmatrix} \cos\theta_2 & -\sin\theta_2 & 0 & l_2 \cos\theta_2 \\ \sin\theta_2 & \cos\theta_2 & 0 & l_2 \sin\theta_2 \\ 0 & 0 & 1 & 0 \\ 0 & 0 & 0 & 1 \end{bmatrix}$$

$$A_2^3 = \begin{bmatrix} \cos\theta_3 & -\sin\theta_3 & 0 & l_3 \cos\theta_3 \\ \sin\theta_3 & \cos\theta_3 & 0 & l_3 \sin\theta_3 \\ 0 & 0 & 1 & 0 \\ 0 & 0 & 0 & 1 \end{bmatrix}
\quad
A_3^4 = \begin{bmatrix} \cos\theta_4 & 0 & -\sin\theta_4 & l_4 \cos\theta_4 \\ \sin\theta_4 & 0 & \cos\theta_4 & l_4 \sin\theta_4 \\ 0 & -1 & 0 & 0 \\ 0 & 0 & 0 & 1 \end{bmatrix}$$

$$A_4^5 = \begin{bmatrix} \cos(90+\theta_5) & 0 & \sin(90+\theta_5) & 0 \\ \sin(90+\theta_5) & 0 & -\cos(90+\theta_5) & 0 \\ 0 & 1 & 0 & 0 \\ 0 & 0 & 0 & 1 \end{bmatrix}
\quad
A_5^6 = \begin{bmatrix} \cos\theta_6 & -\sin\theta_6 & 0 & 0 \\ \sin\theta_6 & \cos\theta_6 & 0 & 0 \\ 0 & 0 & 1 & l_5 + l_6 \\ 0 & 0 & 0 & 1 \end{bmatrix}$$

FIG.9

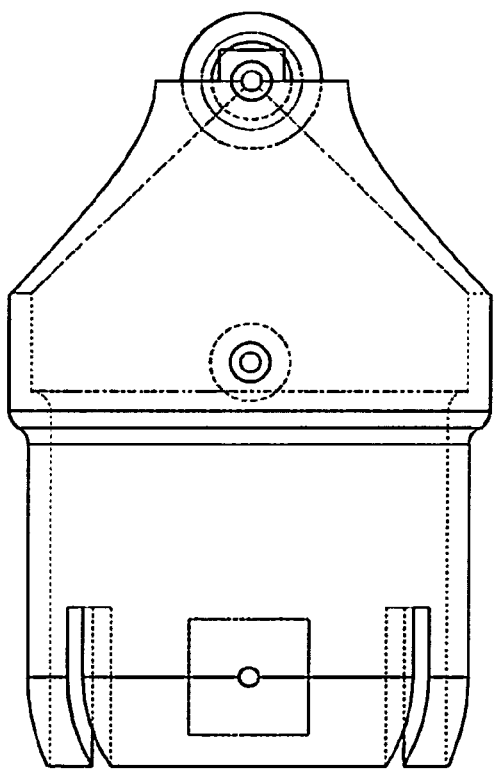
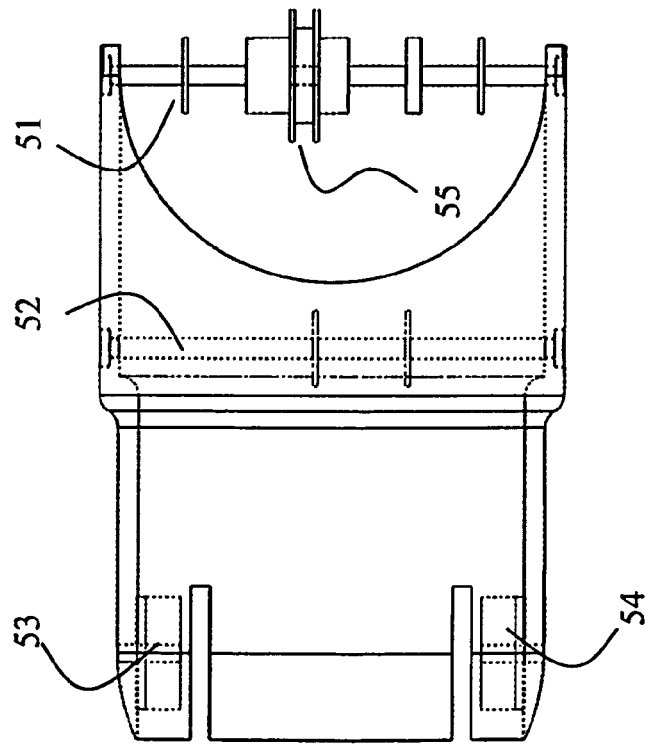
Link 2   Bottom Plane View (Left)   Left Side Plane View (Right)
FIG. 20

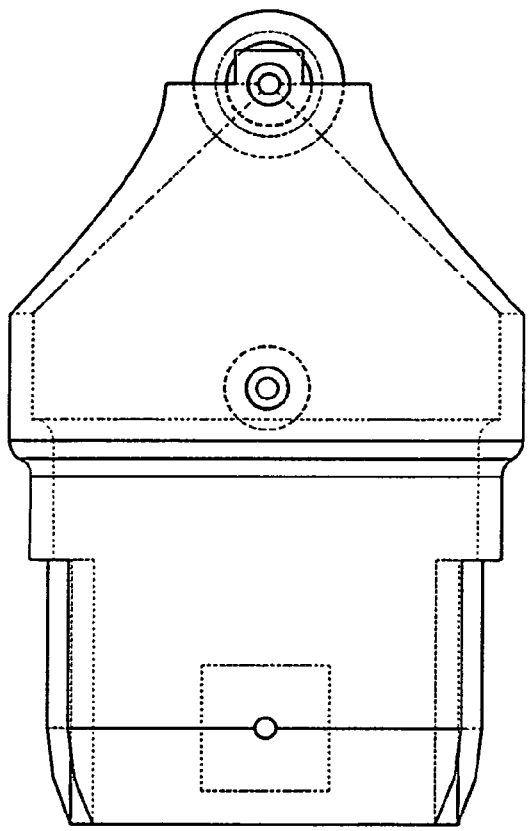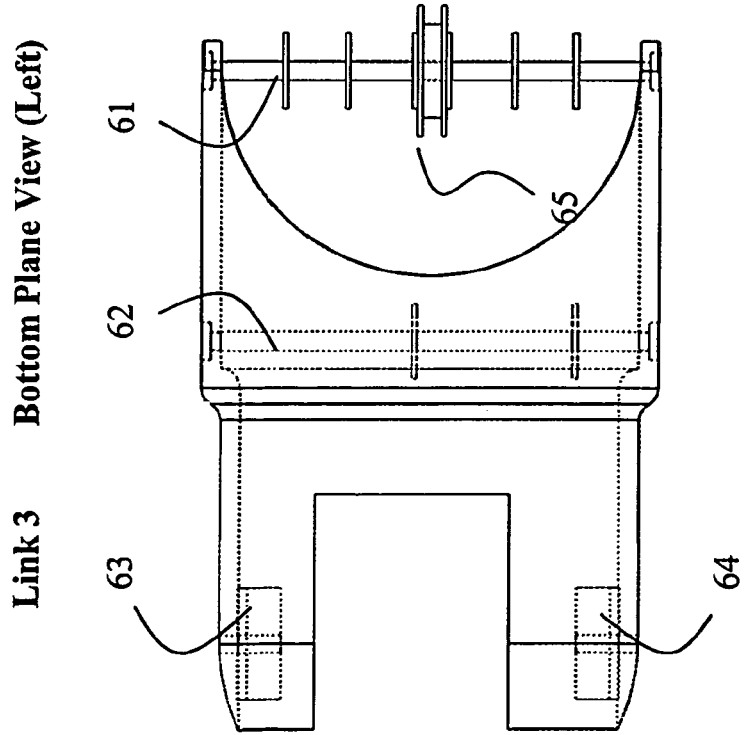
FIG.22

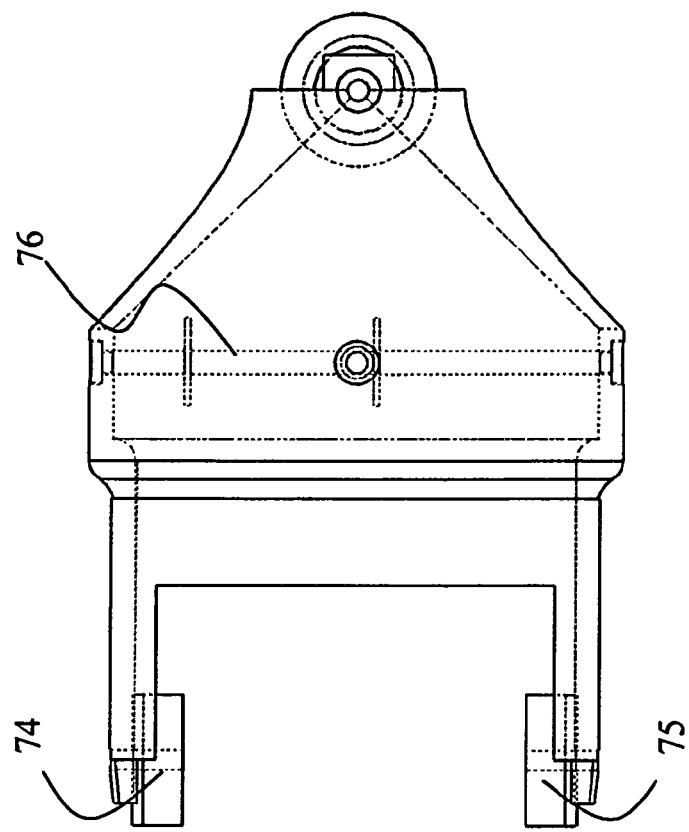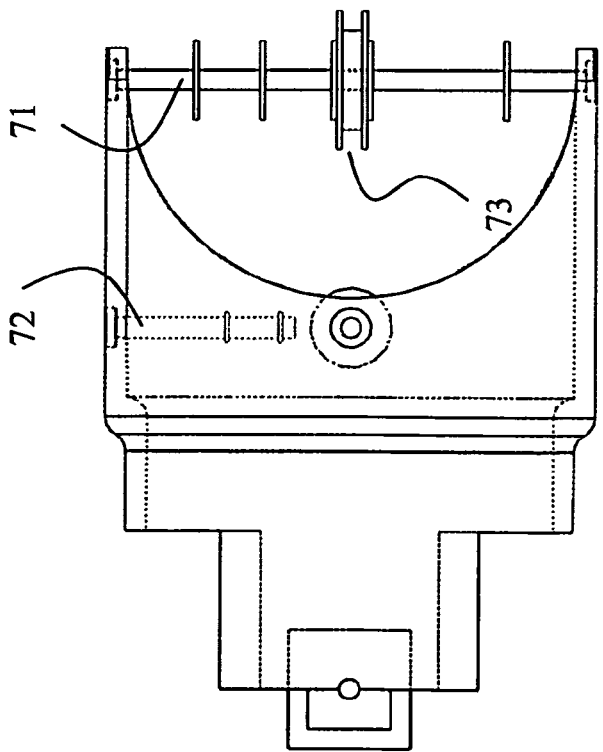
FIG. 24

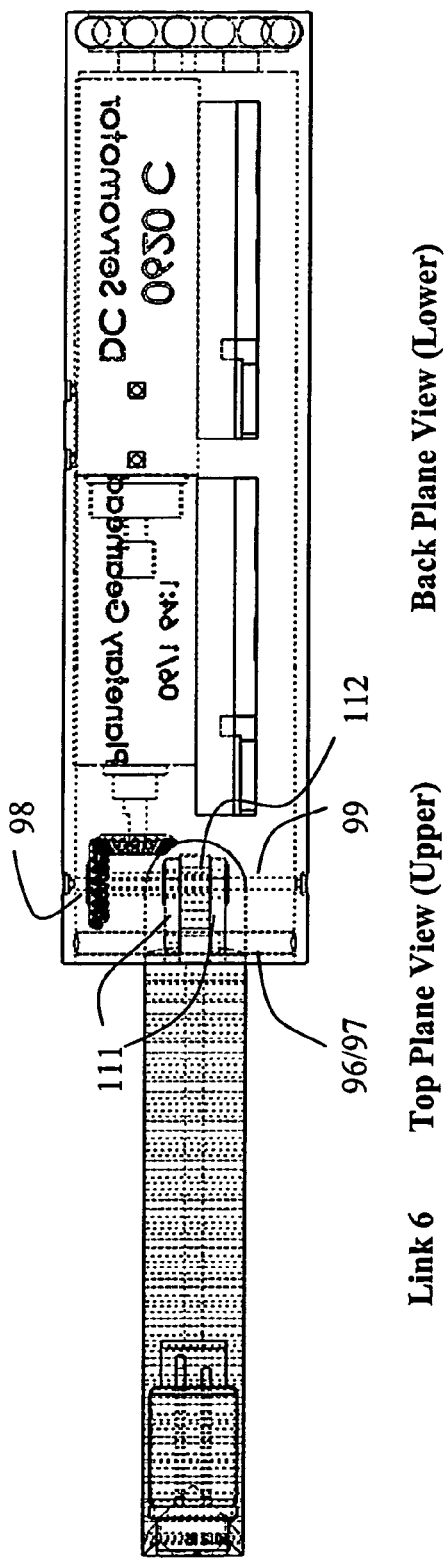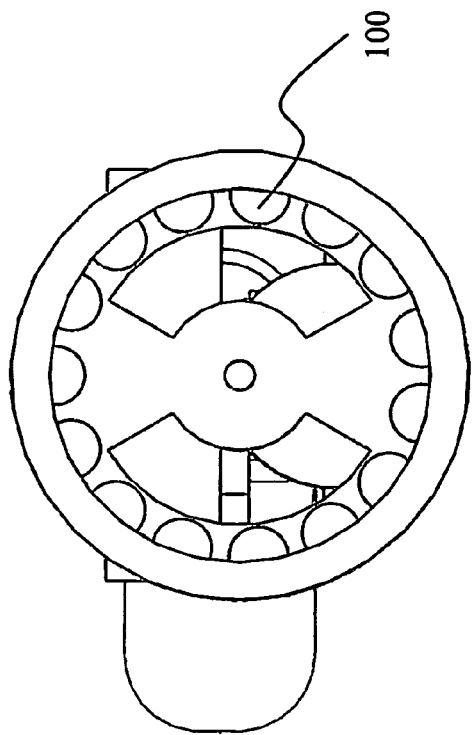
FIG.29

ROBOTIC MODULE FOR NATURAL ORIFICE TRANSLUMINAL ENDOSCOPIC SURGERY (NOTES)

STATEMENT REGARDING FEDERALLY SPONSORED RESEARCH OR DEVELOPMENT

This invention was made with Government support under Contract No. W81XWH-09-C-0161 awarded by the U.S. Army, Telemedicine and Advanced Technology Center (TATRC), 1054 Patchel Street, Fort Detrick, Fredrick, Md. 21702. The Government has certain rights to this invention.

BACKGROUND OF THE INVENTION

1. Field of Invention

This present invention provides a miniature in-vivo robotic module to be used for conducting dexterous manipulations in a patient's abdominal cavity as part of Natural Orifice Transluminal Endoscopic Surgery (NOTES). The robotic module is a serial manipulator consisting of six actively controllable rotational degrees of freedom (DOF), thereby enabling an end effector equipped with a laparoscopic type instrument to assume a commanded position and orientation within the robot's workspace. This module may be anchored and guided to a designated location along the inner abdominal cavity wall via magnetic coupling forces imposed by magnets that are fixed to a different rigid and precise robotic manipulator located external to the patient. This present invention relates to the mechanical design, configuration, and functions of the in-vivo robotic module.

2. Description of Related Arts

Natural Orifice Transluminal Endoscopic Surgery has recently emerged as a step beyond laparoscopic methods for minimally invasive surgery (MIS), and often consists of surgery performed by passing an endoscope with tools through a natural orifice and into the abdominal or peritoneal cavities. A limited number of successful procedures have been documented involving transgastric and transvaginal appendectomies, transgastric and transvaginal cholecystectomies, and a transgastric peritoneoscopy. The majority of clinical trials have been performed on animal models, although a limited amount of human work has also been carried out. Transgastric approaches require instruments to be sent through the mouth, down the esophagus, and into the stomach. Once inside the stomach, a small incision is made for peritoneal access. However, secure closure of the access site is critically important such that anastomotic leaks do not occur. On the other hand, transvaginal approaches are popular as secure closure of the colpotomy wound can be accomplished using conventional methods.

Benefits of NOTES include a reduction in complications from wound infections, faster recovery times, generally less pain, better cosmesis, and a reduction in the need for postoperative care. However, potential barriers to clinical practice identified by the American Society of Gastrointestinal Endoscopy (ASGE) and the Society of American Gastrointestinal and Endoscopic Surgeons (SAGES) include access to the peritoneal cavity, secure internal wound closure (especially gastric and intestinal), prevention of infection, proper suturing, maintaining the desired spatial orientation and visualization, management of intraperitoneal complications, physiologic untoward events, compression syndromes, the need for multidisciplinary training, and so on. Such challenges are compounded by the fact that there is no unifying architecture and multitasking platform for bringing together the existing relevant technologies. Due to the difficulty in developing techniques and technologies for overcoming these barriers, the NOTES surgical practice is still widely considered to be very much in its infancy.

There currently exist a limited number of endoscopic and robotic related NOTES navigation systems and platforms in either the prototype or preclinical stages. There are generally three categories of navigation platforms that have been developed. First, there are endoscope-based platforms, which include redesigned endoscopes such as NeoGuide (NeoGuide Medical Systems, USA), Transport™ and Cobra (USGI Medical, USA), and R-Scope (Olympus Medical Systems, Japan). Then, there are robotic-based platforms such as the master-slave surgical system (Nanyang Technological University, Singapore and National University of Singapore, Singapore) and ViaCath (EndoVia Medical, USA). Finally, there is the use of cooperative micro robots (Nebraska Surgical Solutions, USA). The 2-DOF planer manipulator micro-robot from Nebraska Surgical Solutions is the closest related device to the present invention; however, it is still significantly different in its functionalities and mechanical design.

Although each type of platform device has its relative advantages, there are several prevalent limitations, among which, include the inability to manipulate tissue with the required dexterity and forces, insufficient triangulation and maneuvering capability, and instruments with dimensions unacceptable for widespread clinical use. With the endoscope-based platforms, long and flexible instrumentation must be used. However, it is very difficult to achieve the desired forces, and small diameters prevent triangulation of the flexible instruments within the endoscope tool channels. For these such reasons, there is a lack of available flexible instruments, and several breakthroughs are still required for overcoming their limitations. Furthermore, the navigation platforms of all three categories generally have outer diameters (OD) that are prohibitively large and limit clinical potential. For example, redesigned endoscopes have ODs around 16 mm, whereas the micro-robots have ODs anywhere between 16 to 21 mm.

Based on the current state of NOTES, the Telemedicine and Advanced Technology Center (TATRC) is investing in new robotic systems that enable this procedure type and improve the surgical care of warfighters and their families. It is envisioned that to achieve extensive application of NOTES for improving the cost, quality, and access to surgical care, a novel and modular platform is necessary.

SUMMARY OF THE PRESENT INVENTION

It is a main objective of the present invention to provide a miniature in-vivo robotic module to be used for conducting dexterous manipulations on target organs or other entities in a patient's abdominal or peritoneal cavity as part of Natural Orifice Transluminal Endoscopic Surgery. The robotic module is wirelessly teleoperated, where commands from a surgeon that have been processed by a computer external to the patient are wirelessly transmitted to antennas and transceivers installed in the robotic module.

Another objective of the present invention is to provide a modular and flexible design such that a team of robotic modules dedicated to different tasks can be deployed, where each individual module incorporates a basic set of common components and capabilities along with additional functionalities afforded depending on the specific use. Common components include microcontrollers (MCU) and wireless transceivers, antennas, geared micro-motors with encoders, printed circuit boards (PCB), lithium ion polymer batteries, and magnetic docking interfaces. Specific use components depend on the surgical task considered and include different sensor suites (e.g. with sensors such as an infrared temperature sensor) as well as laparoscopic tools such as atraumatic graspers, monopolar or bipolar electrocautery, endoloops, electrosurgical bipolar snares, etc.

Another objective of the present invention is to provide a robotic module that is capable of navigating an endoscopic type overtube starting from a natural orifice (e.g. peroral insertion) or preexisting wound, through regions such as the esophagus and stomach, and finally into the abdominal cavity. This requires that the module geometry to be acceptable for clinical application in NOTES procedures, which imposes constraints on the maximum outer diameter and links lengths of the manipulator as well as requiring cylindrical shapes for minimizing the presence of sharp edges.

Another objective of the present invention is to provide a robotic module design with a magnetic anchoring and guidance system (MAGS) wherein once the module has navigated through the overtube and is placed in the abdominal cavity, it may then be anchored and guided (via translational and rotational gross motion of the entire device) to a designated location via magnetic coupling forces between internal embedded magnets and magnets fixed to the end effector of an external (with respect to the patient) rigid and precise robotic manipulator.

Another objective of the present invention is to provide a robotic module design consisting of a serial manipulator with seven cylindrical links and six actively controllable rotational degrees of freedom such that the necessary maneuverability and dexterity requirements may be met. With six rotations available, an end effector may thus assume a commanded position and orientation within the robot's workspace. Considering a docked module and adopting the roll-pitch-yaw (RPY) convention, these DOFs correspond to three pitches, two yaws, and one roll.

Another objective of the present invention is to provide a clinically acceptable robotic module design wherein portions of the robotic module interfacing with the internal body cavity environment meet FDA standards and sterilization requirements.

Another objective of the present invention is to provide sufficient forces on tissue and other entities as part of NOTES procedures. This is enabled by the use of geared motors, rigid links, and a laparoscopic type instrument fixed to the end effector without relying on flexible components that would otherwise diminish the forces.

Another objective of the present invention is to provide a design that minimizes the overall weight of the robotic module such that the force and torque requirements on the coupling magnets and micro-motors are eased. An internal remote cable-drive transmission system reduces the number of heavy components such as motors while saving space that can instead be allocated for other components such as electronic circuit boards and sensors. Instead of integrating six motors as would be necessary for direct actuation of the joints, with remote actuation only four motors are required. Moreover, motors are not needed in three of the links, which facilitates shorter link lengths for an overall more compact and therefore clinically useful robotic module.

Another objective of the present invention is to provide a robotic module design that is streamlined for low-cost production wherein a heavy reliance is placed on the integration of easily available commercial-off-the-shelf (COTS) components and straightforward mechanical components such as pulleys, pins, shafts, gears, etc.

According to the present invention, the foregoing and other objects and advantages are attained by a wirelessly teleoperated in-vivo robotic module tailored for performing surgical functions of relevance for Natural Orifice Transluminal Endoscopic Surgery, comprising:

a robotic serial manipulator with seven connected cylindrical links and six controllable rotational degrees of freedom for the joints wherein, (1) link 0 (referred to as the battery-base link) contains a magnetic docking interface with a cylindrical neodymium iron boron (NdFeB) permanent magnet, lithium-ion polymer batteries, a circular printed circuit board with a microcontroller/wireless transceiver chipset and motor drivers, a compact chip antenna, and a torsion spring damper mechanism;

(2) link 1 (referred to as the motor-base link) contains another magnetic docking interface with rectangular NdFeB permanent magnets, the torsion spring damper mechanism, several shafts and pins for fixing components to the cylindrical link body, a low-torque DC geared micro-motor with an encoder for transmission selection, a higher-torque DC geared micro-motor with an encoder for transmission actuation, a pair of joint damping blocks for eliminating undesirable joint motion, and a portion of the remote cable-drive transmission system comprised of a transmission selection mechanism, several pulleys, shafts, cables, and gears (both bevel and spur types);

(3) link 2 contains a pair of joint damping blocks as well as components for realizing a portion of the remote cable-drive transmission system including several pulleys, shafts, and cables.

(4) link 3 contains a pair of joint damping blocks as well as components for realizing a portion of the remote cable-drive transmission system including several pulleys, shafts, and cables.

(5) link 4 contains a pair of joint damping blocks as well as components for realizing a portion of the remote cable-drive transmission system including several pulleys, bevel gears, shafts, and cables.

(6) link 5 contains a DC geared micro-motor with sensor feedback (but does not use a separate encoder), several shafts and pins for fixing components to the cylindrical link body, a printed circuit board with a microcontroller/wireless transceiver chipset and motor drivers, a compact chip antenna, a pulley, shaft, and cable for completing the remote cable-drive transmission system, and a ball bearing track; and (7) link 6 contains a DC geared micro-motor with sensor feedback (but does not use a separate encoder), lithium-ion polymer batteries, several shafts and pins for fixing components to the cylindrical link body, a ball bearing track with spherical bearings and, in the present embodiment, a mechanism consisting of a set of bevel gears and shafts for fixing the link with either a COTS laparoscopic grasper or a custom designed grasper. This invention provides a custom grasper design consisting of a straight single-action grasping forceps with several triangular teeth.

the said robotic serial manipulator consisting of the said cylindrical links with six controllable rotational degrees of freedom which, when considering a docked module and defining the yaw rotation axis as normal to the skin wall are comprised of:

(1) gross yaw rotation (DOF1) of the entire robotic module as controlled by two external magnets fixed to the end effector of an external positioning manipulator;

(2) pitch rotation (DOF2) between links 1 and 2 as controlled by the DC micro-motors of the motor base link and the $1^{st}$ transmission cable set;

(3) pitch rotation (DOF3) between links 2 and 3 as controlled by the DC micro-motors of the motor base link and the $2^{nd}$ transmission cable set;

(4) pitch rotation (DOF4) between links 3 and 4 as controlled by the DC micro-motors of the motor base link and the $3^{rd}$ transmission cable set;

(5) yaw rotation (DOF5) between links 4 and 5 as controlled by the DC micro-motors of the motor base link and the $4^{th}$ transmission cable set; and (6) roll rotation (DOF6) between links 5 and 6 as controlled by the DC micro-motor of link 5.

wherein an additional passive yaw degree of freedom (DOF0) is used for rotation between links 0 and 1 during module overtube insertion (necessary for following a complex insertion trajectory), but is constrained after magnetic docking occurs prior to starting a procedure;

wherein additional translational degrees of freedom may be provided by the external magnets during global positioning of the robotic module; and wherein an additional degree of freedom may be considered as part of the opening and closing motion of the laparoscopic type grasper (DOF7).

Still further objects and advantages will become apparent from a consideration of the ensuing description and drawings.

These and other objectives, features, and advantages of the present invention will become apparent from the following detailed description, the accompanying drawings, and the appended claims.

BRIEF DESCRIPTION OF THE DRAWINGS

FIG. 9 presents the general form for the homogeneous transformation matrix as well as the six specific matrices that relate each local coordinate frame of this robotic module.

FIG. 20 is a CAD rendering of link 2 as viewed from the bottom and left side planes with hidden lines. Internal components are numbered.

FIG. 22 is a CAD rendering of link 3 as viewed from the bottom and left side planes with hidden lines. Internal components are numbered.

FIG. 24 is a CAD rendering of link 4 as viewed from the bottom and left side planes with hidden lines. Internal components are numbered.

FIG. 29 is a CAD rendering of link 6 with a laparoscopic grasper as viewed from the top plane with hidden lines and the back plane without hidden lines. Internal components are numbered.

DETAILED DESCRIPTION OF THE PREFERRED EMBODIMENT

Figure 1:
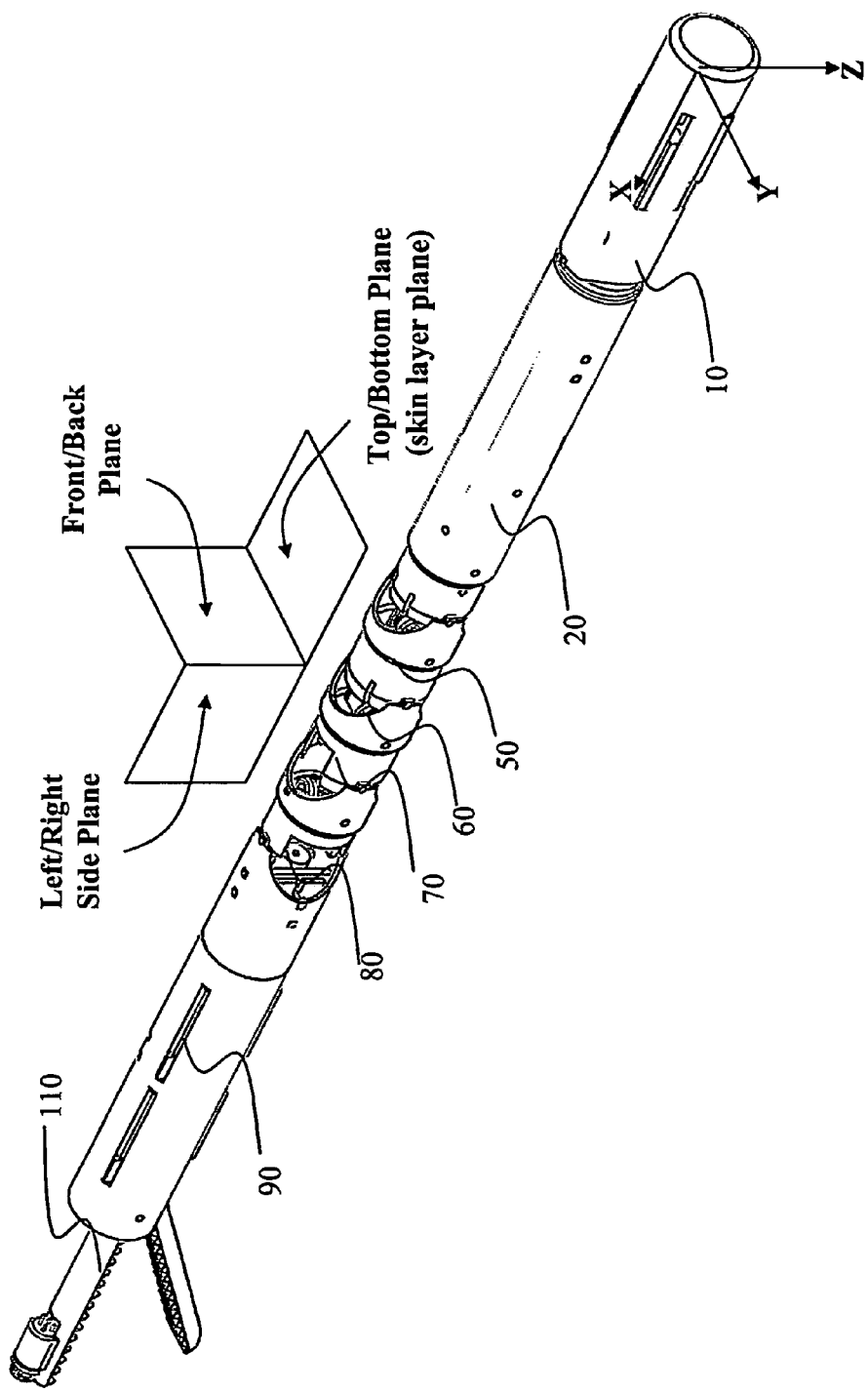
FIG. 1 is a computer aided design (CAD) rendering of the entire robotic module in its insertion mode configuration (i.e. the shape assumed immediately prior to overtube navigation) as viewed from an isometric projection. Major components are numbered and reference planes as well as the global coordinate axis (which is translated in subsequent figures for clarity in presentation) are shown.

Referring to FIG. 1, a robotic module for Natural Orifice Transluminal Endoscopic Surgery (NOTES) according to a preferred embodiment of the present invention is illustrated, which consists of a serial manipulator comprised of seven connected cylindrical links and a specialized laparoscopic grasper. The links have a cylindrical geometry that has been optimized for overtube insertion and for enabling maximum joint range of motions (ROM). Although a small portion of the on-board batteries extend slightly beyond the cylinder surface (by less than 1 mm) with a sterilized and protective sheath covering the module, the outer body then consists of only smooth surfaces without any sharp edges that may otherwise damage tissue. Before being placed in the abdominal or peritoneal cavity, it is necessary for the robotic module to navigate from a natural orifice and then possibly through internal sections of the body such as the esophagus and stomach. An endoscope type overtube can be used for accomplishing this in which the robotic module in its "insertion mode configuration" as depicted in FIG. 1 is sent through the overtube and exits near the target destination. In this configuration, the links are initially parallel to one another and may then rotate with respect to one another as necessary for adhering to the curvature of the path followed.

Figure 2:
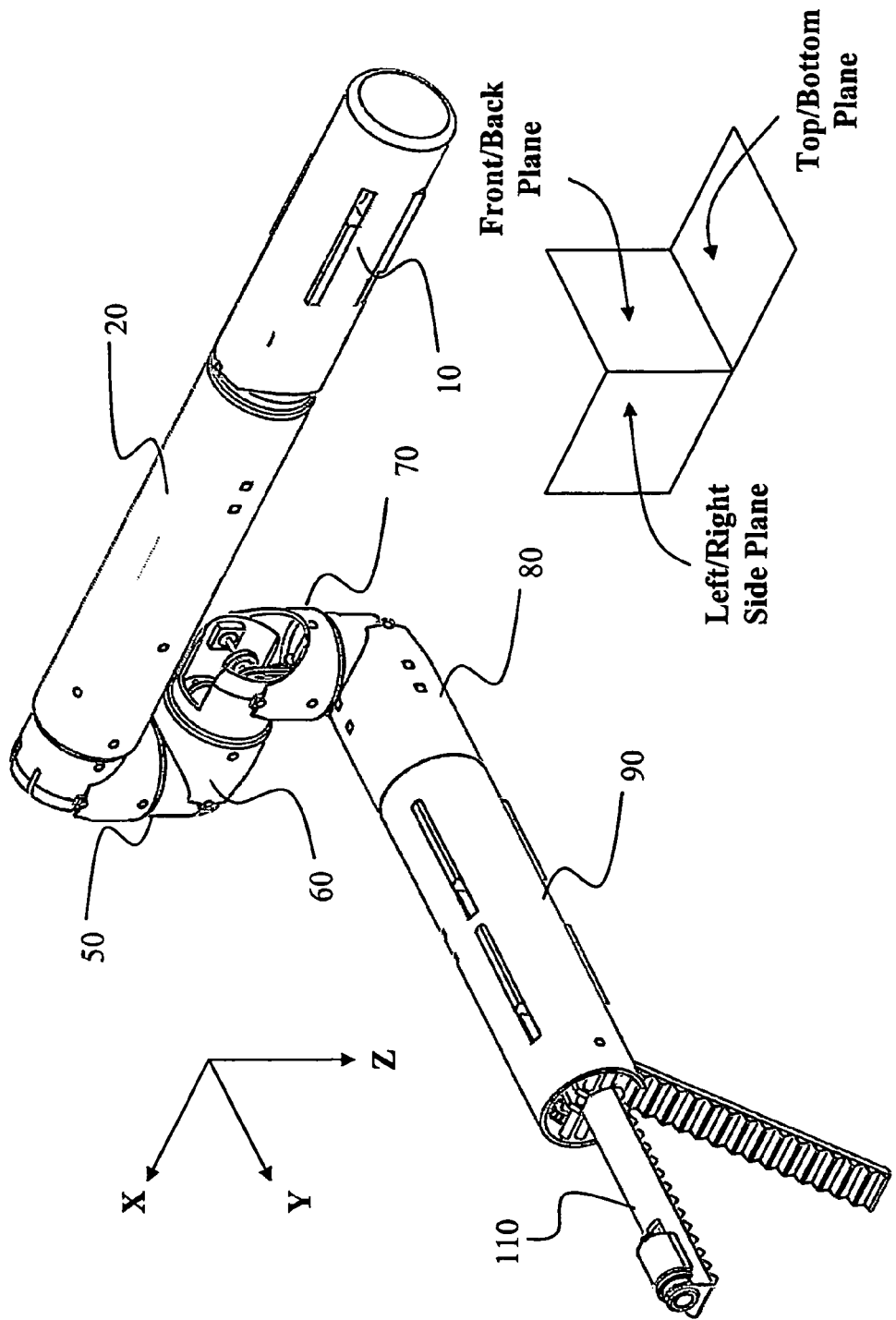
FIG. 2 is a CAD rendering of the entire robotic module in a surgical tasks mode configuration (i.e. any shape assumed where the first two base links are docked to the inner abdominal wall) as viewed from an isometric projection. Major components are numbered and reference planes as well as the global coordinate axis are shown.
Figure 3:
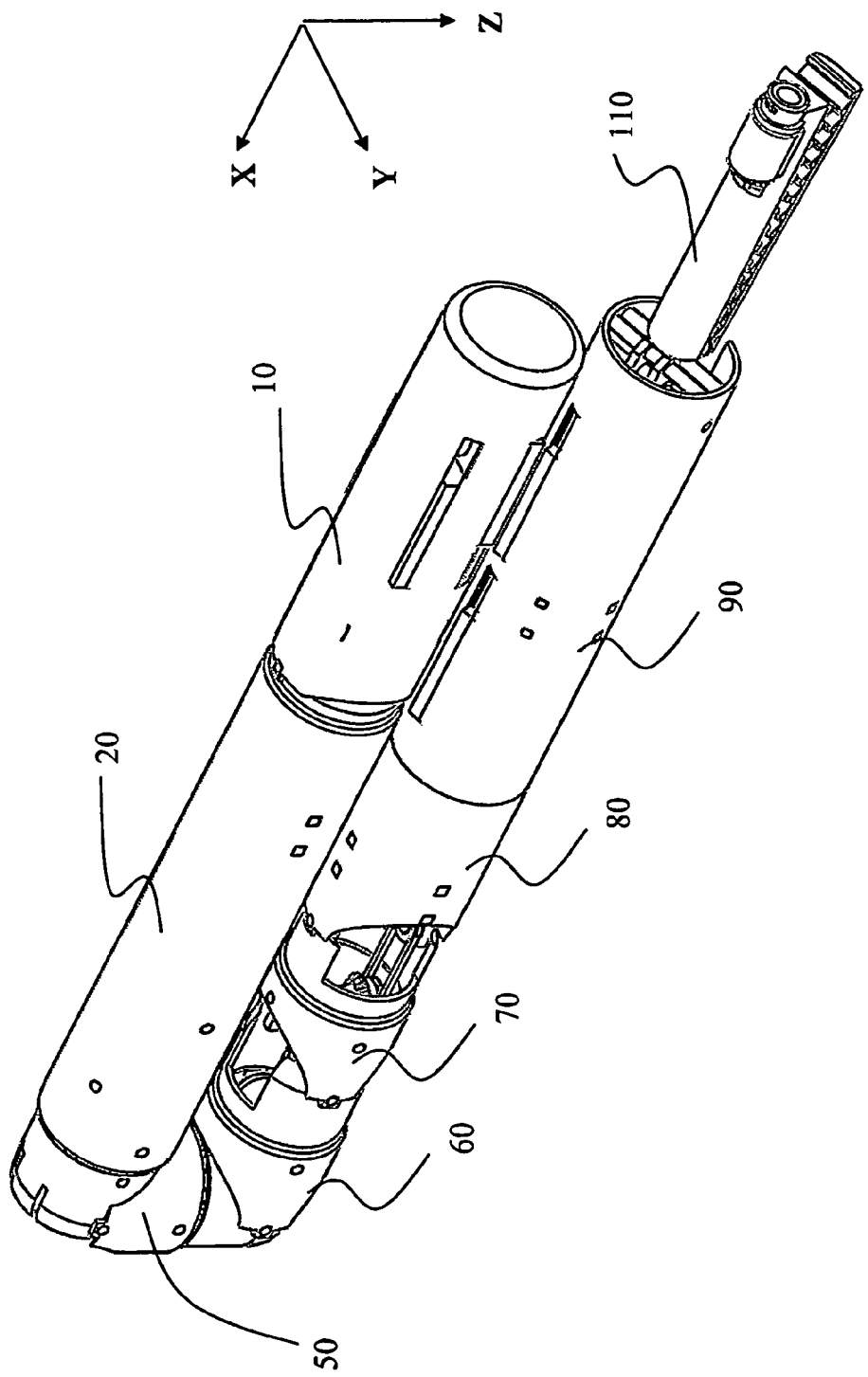
FIG. 3 is a CAD rendering of the entire robotic module in a folded up configuration as viewed from an isometric projection. Major components are numbered and the global coordinate axis is shown.

After arriving at a target destination, the robotic module may be docked to the inner abdominal wall via forces exerted by a Magnetic Anchoring and Guidance System (MAGS) and thereafter assume a position more suitable for performing surgical tasks as depicted in FIG. 2. According to the reference plane convention adopted, the inner skin wall is parallel to the top/bottom plane. The battery-base link (link 0) 10 and the motor base link (link 1) 20 each contain a set of permanent magnets, with each set attracted to two corresponding magnets that are external to the patient and fixed to the end effector of a different robotic positioning manipulator. The coupling forces may be used for navigating the robotic module to a preferred location, performing gross rotations, and then anchoring. The remaining links 50-90 can then move independently based on actuators and control electronics housed within the device. Therefore, the end effector fixed with a laparoscopic type tool 110 such as atraumatic graspers may follow a trajectory for arriving at a desired position and orientation within the robot's workspace. FIG. 3 shows an example of a manipulator configuration that could then be achieved, where it is noted that the ROMs are sufficient for a very compact folding of the device if required for a certain scenario.

Figure 4:
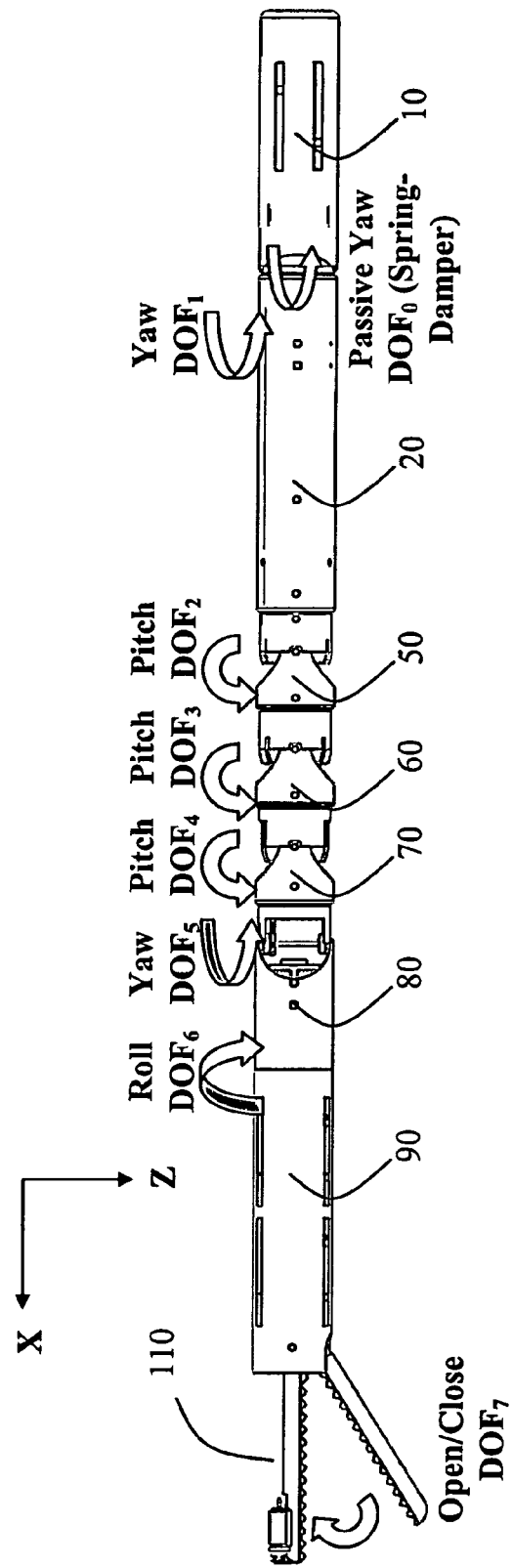
FIG. 4 is a CAD rendering of the entire robotic module in its insertion mode configuration as viewed from the left side plane. Major components are numbered and the manipulator degrees of freedom as well as the global coordinate axis are shown.

Referring to FIG. 4, according to the preferred embodiment, the robotic module is a manipulator consisting of the following labeled six rotational degrees of freedom: (1) yaw DOF1; (2) pitch DOF2; (3) pitch DOF3; (4) pitch DOF4; (5) yaw DOF5; and (6) roll DOF6. The roll-pitch-yaw (RPY) convention is illustrated by arrows depicting the degrees of freedom, where it is noted that the axis of rotation for yaw is defined as along the Z direction. The yaw DOF1 causes gross rotation of the entire device, and is enabled by rotation of the external magnets and the coupling forces with the internal magnets embedded in the module. The center of rotation is offset from the joint connecting link 0 10 and link 1 20. Pitch DOF2, pitch DOF3, and pitch DOF4 occur at the joints bridging link 1 20 with link 2 50, link 2 50 with link 3 60, and link 3 60 with link 4 70 respectively. Yaw DOF5 occurs at the joint between link 4 70 with link 5 80. These four DOFs are controlled by a set of DC micro-motors located at the motor base link 20, and are remotely actuated based on cable-drive transmissions. Each may be actuated only one at a time, the reason for which will become clear with subsequent descriptions of the preferred embodiment. Next, the roll DOF6 occurs between link 5 80 and link 6 90 and is directly actuated by an internal micro-motor located at link 5. In addition to these controllable degrees of freedom, an additional DOF exists due to yaw rotation between links 0 and 1 that is allowed during module overtube insertion. This joint is necessary since if these two links otherwise formed a single rigid body, the resulting length would be too great for following many complex insertion trajectories. This degree of freedom is characterized by a spring and damper mechanism (for providing a damped restoring force) and is not controlled by any actuator. It is therefore considered to be a passive DOF. Upon magnetic docking, since two sets of magnets are placed in each base link, relative rotations at this joint can then be suppressed and the two base links thereafter may act as a single rigid body. According to the present embodiment depicted in FIG. 4, yet another degree of freedom may be considered as part of the opening and closing motion of the laparoscopic grasper (DOF7). Finally, translational degrees of freedom along the X and Y directions may be provided by the external magnets during global positioning of the robotic module.

Figure 5:
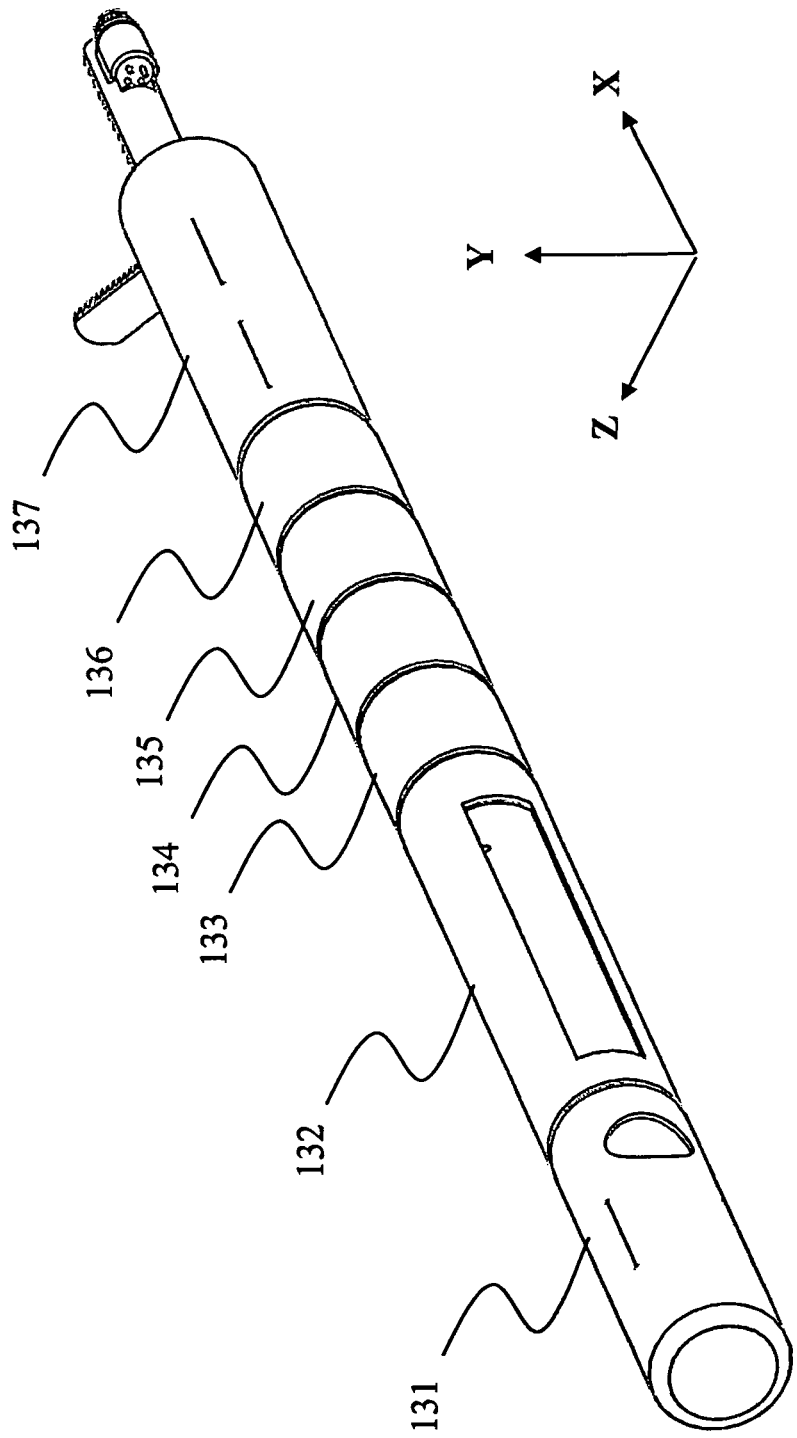
FIG. 5 is a CAD rendering of the entire robotic module in its insertion mode configuration with a set of protective sheath components as viewed from an isometric projection. Major components are numbered and the global coordinate axis is shown.

Referring to FIG. 5, the robotic module may be fitted with a sterilized protective sheath for providing a clinically acceptable interface with the in-vivo environment. Without a sheath, the module has many open areas (especially when the links move relative to one another) where bacteria could build up and result in infections within the patient. Since it would be difficult to sufficiently sterilize all of these locations, a flexible sheath is preferred that can cover the robotic module. The sheath must be flexible enough to handle the full range of joint motions, but must also be firmly sealed to the module. For best accomplishing this, the sheath is divided into seven separate sections 131-137 where each section is flexible enough to allow the complete range of rotation for only a single joint. The end locations of each section are offset from each joint. The method of dividing the sheath into several components is based on the acknowledgment that it would be difficult to find a material flexible enough to cover the full range of rotations of all of the joints combined. Since magnetic coupling forces would be reduced when using the sheath, areas are cut out in the first two sections 131 and 132 as to not cover up the magnets.

Figure 6:
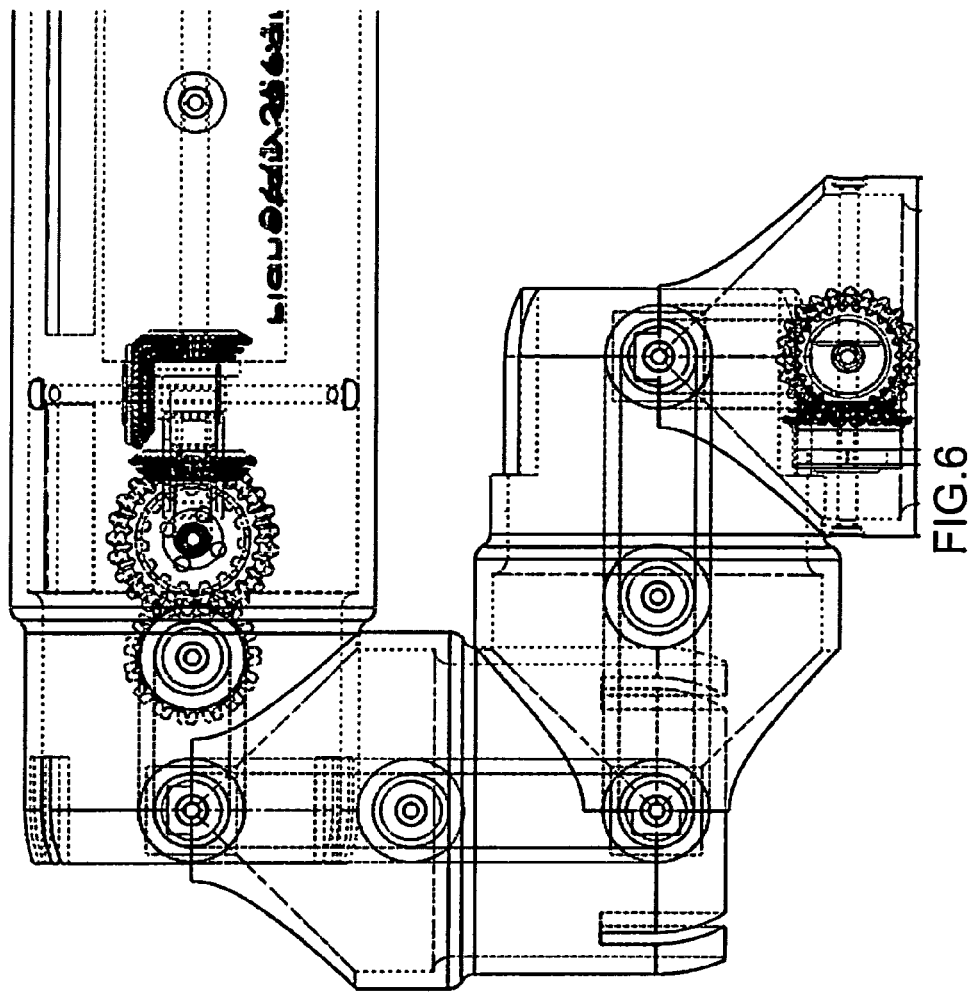
FIG. 6 is a CAD rendering of the robotic module's links 1 (partial), 2, 3, and 4 (partial) with maximum rotations for pitch DOF2, pitch DOF3, and pitch DOF4 as viewed from the left side plane with hidden lines.
Figure 7:
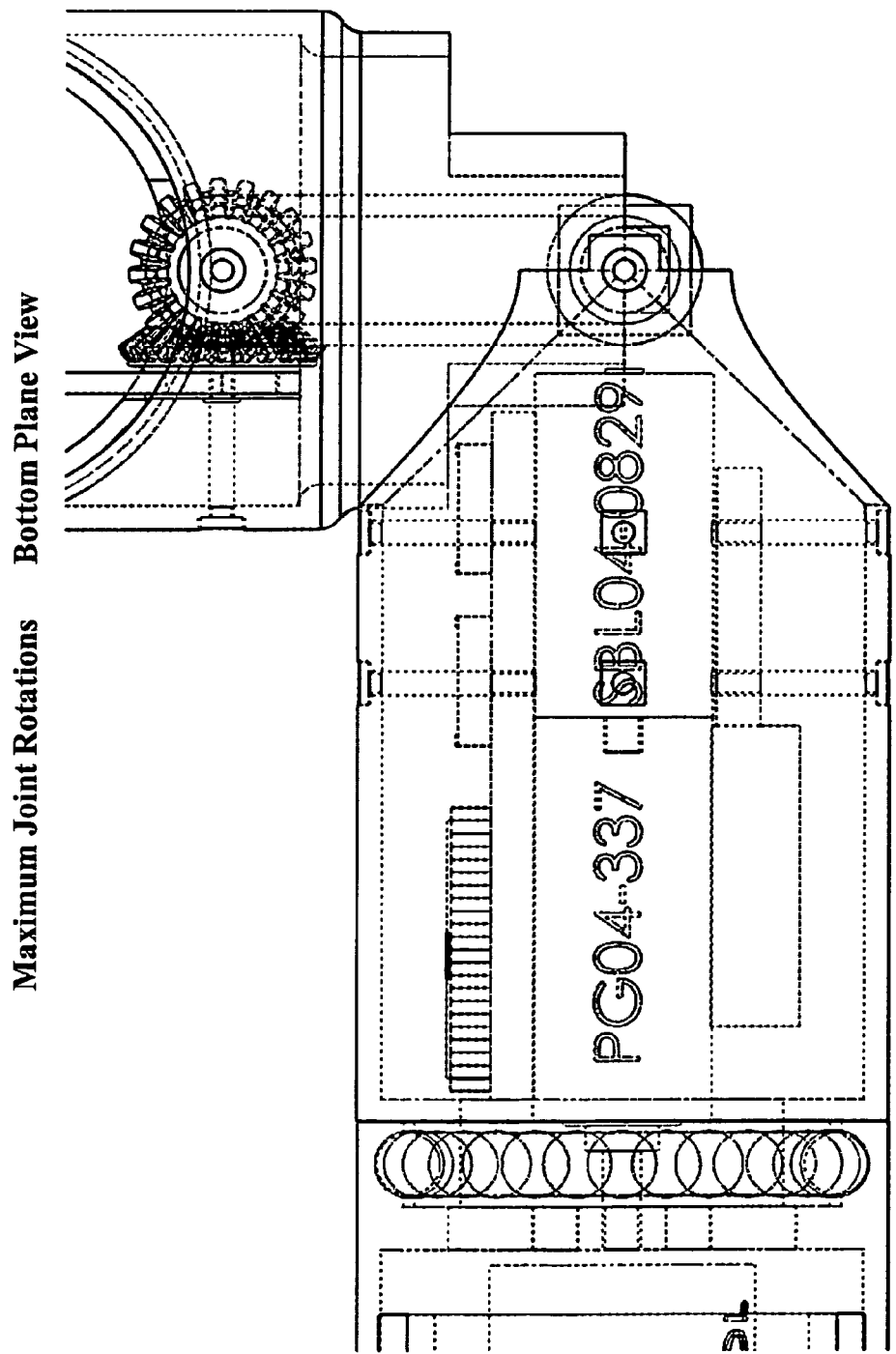
FIG. 7 is a CAD rendering of the robotic module's links 4 (partial) and 5 with a maximum rotation for yaw DOF5 as viewed from the bottom plane with hidden lines.

According to the preferred embodiment as discussed in the previously referenced figures, the robotic module has a 12 mm outer diameter (OD) (slightly larger when using the protective sheath) and the following link lengths: (1) link 0=40 mm; (2) link 1=61 mm; (3) link 2=15 mm; (4) link 3=15 mm; (4) link 4=15 mm; (5) link 5=20 mm; and (6) link 6=48 mm (78 mm with the custom laparoscopic grasper) for a maximum total length of 244 mm. Upon comparison, a miniature robot by Nebraska Medical Center, University of Nebraska, has a cross sectional area of 14×17 mm and a total length of 186 to 250 mm (variable due to the use of translational joints). If desired, the length of the module in the present invention can be further reduced by the selection of components and motors that are different from the commercial-off-the-shelf (COTS) solutions presented in future paragraphs. Moreover, it should be noted that the rotational joints allow for the module to assume more compact configurations as depicted in FIG. 2 and FIG. 3. Specifically, the maximum range of motion for each joint is given as follows: (1) yaw DOF1=±180°; (2) pitch DOF2=±90°; (3) pitch DOF3=±90°; (4) pitch DOF4=±90°; (5) yaw DOF5=±90°; and (1) roll DOF6=±180°. FIG. 6 depicts the maximum relative rotations that are possible with the pitch degrees of freedom and FIG. 7 shows the maximum relative rotation for the yaw DOF5. The cylindrical link geometry has been optimized such that these positions may be assumed without any interferences or collisions among neighboring links and/or between the links and internal components such as pulleys, cables, and so on.

Figure 8:
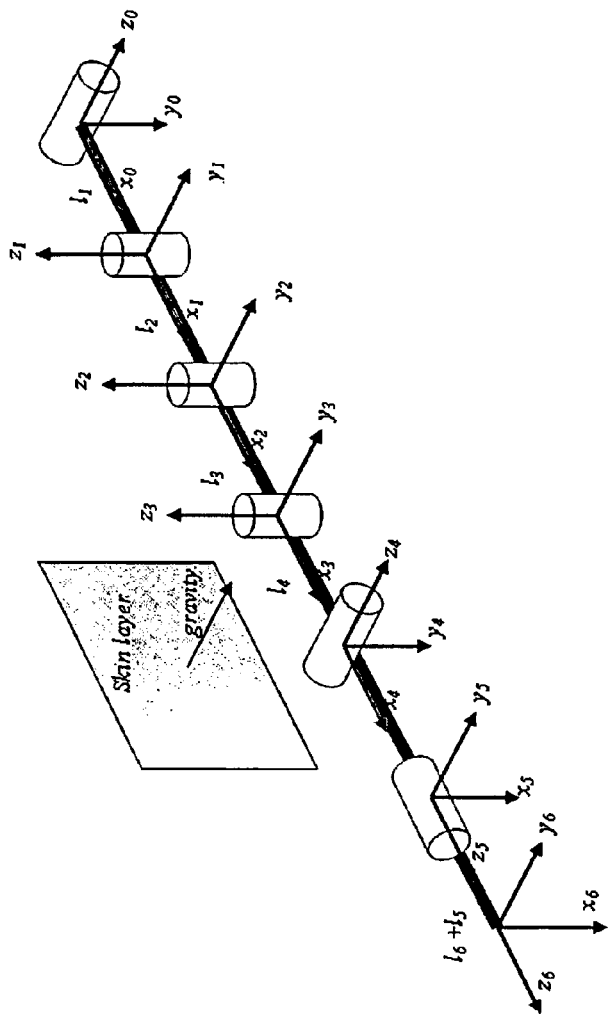
FIG. 8 contains an illustration of the robotic module's kinematic structure along with the local coordinate frames and labeled parameters. A table is also included comprised of the Denavit-Hartenberg (D-H) structural kinematic parameters.

According to the degrees of freedom presented in FIG. 4, the robotic module's kinematic structure along with the local coordinate frames and labeled parameters is illustrated in FIG. 8. It is noted that this structure is similar to common industrial manipulators (e.g. Cincinnati Milacron) where joint axes $z_1$ (pitch DOF2) and $z_2$ (pitch DOF3) are parallel to one another and perpendicular to $z_0$ (yaw DOF1) and the last three axes, $z_3$ (pitch DOF4), $z_4$ (yaw DOF5), and $z_5$ (roll DOF6) form a spherical wrist (not technically met here since $l_4 \neq 0$). This configuration has been documented to provide a large freedom of movement in a compact space which is what motivated the design. A table is also included comprised of the Denavit-Hartenberg (D-H) structural kinematic parameter values for the robotic module. For kinematic derivations, it is necessary to group links 5 and 6 into $l_6$ and let $l_5=0$ (since two links $l_i$ and $l_{i+1}$ separated by a roll joint is equivalent to having a single link $l_i=l_i+l_{i+1}$ with a roll DOF at the joint between $l_{i-1}$ and $l_i$). Also, $l_1$ as defined here is the distance from the center of rotation of yaw DOF1 to the end of the motor base link (link 1) and has a value of 45 mm.

Based on information from FIG. 8, it is straightforward to establish forward kinematic relations such that a set of joint positions can be related to an end effector position and orientation. FIG. 9 includes the general form for the homogenous transformation matrix which transforms the coordinates of a point from frame i−1 to frame i. According to the coordinate frames and D-H parameters in FIG. 8, the six specific matrices that relate each local coordinate frame of this robotic module are then included in FIG. 9 as well. By carrying out successive multiplications of these matrices, a transformation matrix can be determined which takes in the joint angles and the end effector position/orientation relative to its own coordinate system, and uniquely identifies the position and orientation of the end effector in the base coordinate system. In other words, provided the joint angles and link lengths as well as the end effector pose in the $6^{th}$ coordinate frame, the transformation matrix uniquely provides the position of the end effector relative to the $0^{th}$ coordinate frame at the beginning of the manipulator chain.

Although forward kinematics can be used for robotic control over small increments, a more intuitive scheme would involve specifying the desired end effector position and orientation in the base frame and then computing the necessary joint angles and local end effector pose. This is referred to as the problem of inverse kinematics. Finding the inverse kinematic relations is far from trivial as a solution does not always exist, and even if it does is often degenerate, as different combinations of joint angles may result in the same position and orientation. There may even be an infinite number of solutions for some cases as at manipulator singularities. For the robotic module structure presented in FIG. 8 an analytical, closed-form solution to the inverse kinematics does not exist. Instead, numerical methods such as involving the pseudoinverse, Jacobian transpose, Levenberg-Marquardt damped least squares, quasi-Newton and conjugate gradient, etc. must be leveraged.

Figure 10:
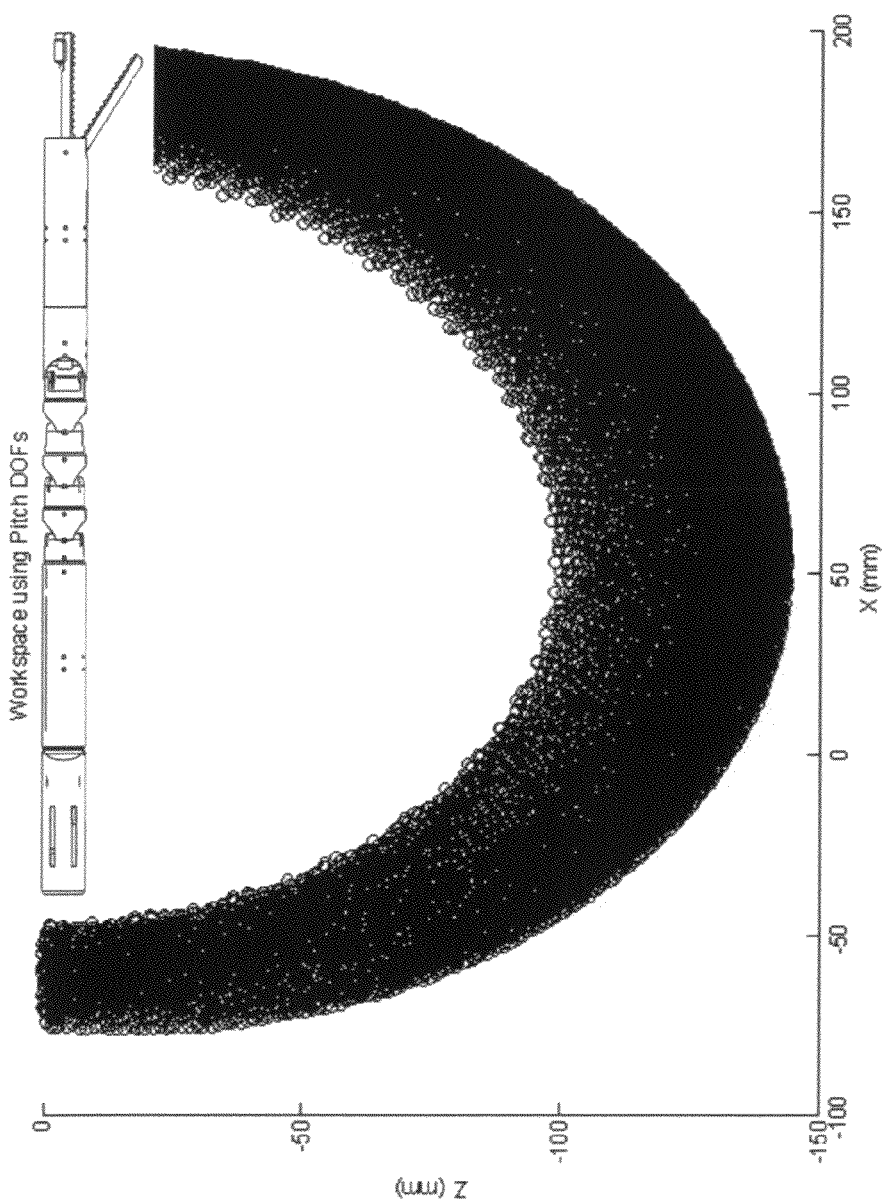
FIG. 10 includes a two-dimensional plot of the manipulator workspace that is achieved by actuation of only pitch degrees of freedom. For better visualization, the manipulator is superimposed on the plot.
Figure 11:
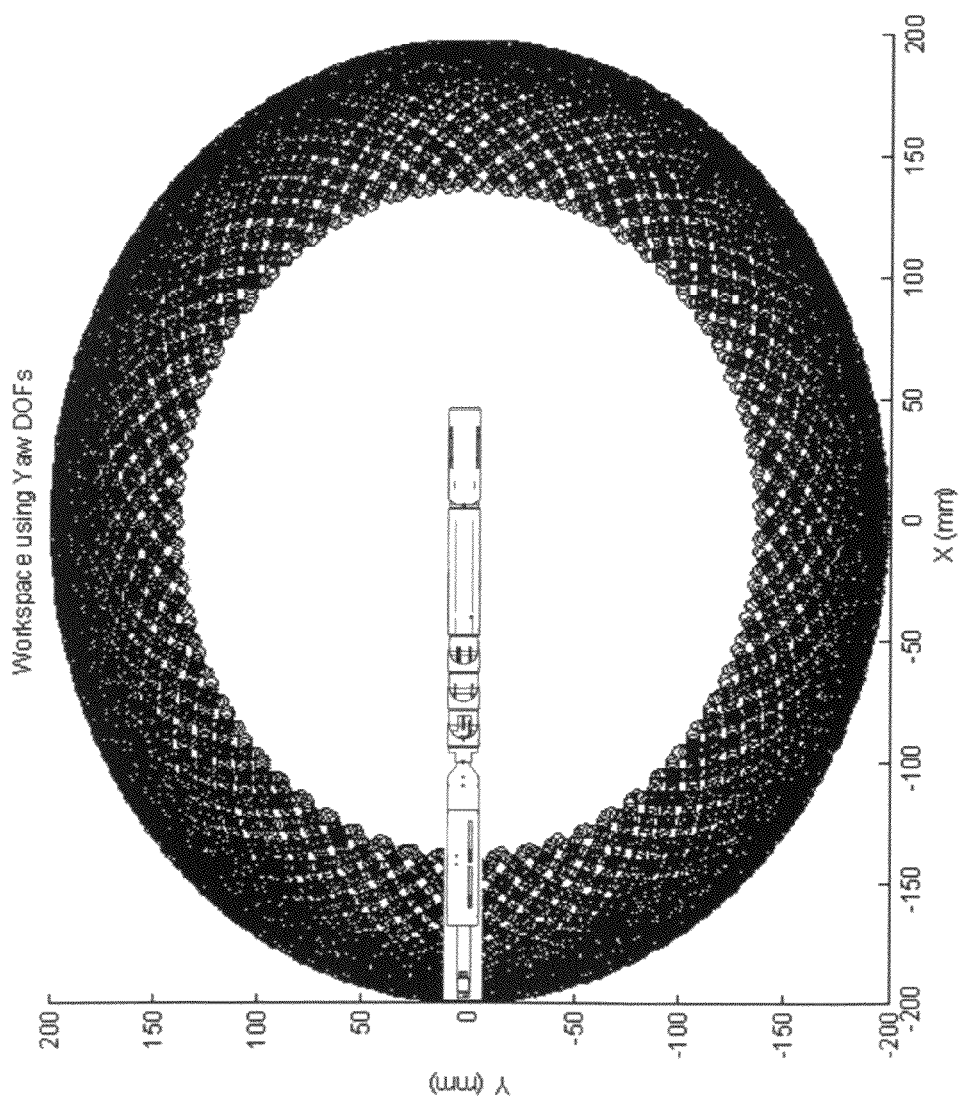
FIG. 11 includes a two-dimensional plot of the manipulator workspace that is achieved by actuation of only yaw degrees of freedom. For better visualization, the manipulator is superimposed on the plot.

Referring to FIG. 10, the workspace for the manipulator that is achieved by actuation of the pitch degrees of freedom has been determined. A workspace is defined as the set of all points that can be reached by the end effector of a manipulator arm. Conversely, the deadspace is defined as the points that cannot be reached by the end effector. In FIG. 10, the pitch workspace is defined by the shaded region, and the manipulator is shown for facilitating analysis. The inner abdominal wall presents a boundary at Z=0 and therefore points at Z>0 cannot be reached by the end effector. Next, referring to FIG. 11, the workspace that is achieved by actuation of only yaw degrees of freedom is depicted by the shaded region and with the manipulator superimposed on the plot. Although not shown, when working with all degrees of freedom, the 3-dimensional workspace logically forms a bowl type shape with some thickness. It should be noted that this workspace does not consider gross translations of the robotic module which are possible with the external magnets and which would expand the workspace. Instead, a module mounted via magnetic anchoring is considered and the locations that can then be achieved by the end effector based on only rotational DOFs comprise the workspace area.

The design, configuration, and functionalities of the miniature in-vivo robotic module have evolved such that dexterous manipulations on organs and other target entities in a patient's abdominal or peritoneal cavity as part of NOTES can be performed. This has resulted in the definition of seven cylindrical links that comprise the serial manipulator and the components that are housed within each. In the following paragraphs, the design, components, and functions of each cylindrical link are described in detail according to the preferred embodiment of the present invention.

Figure 12:
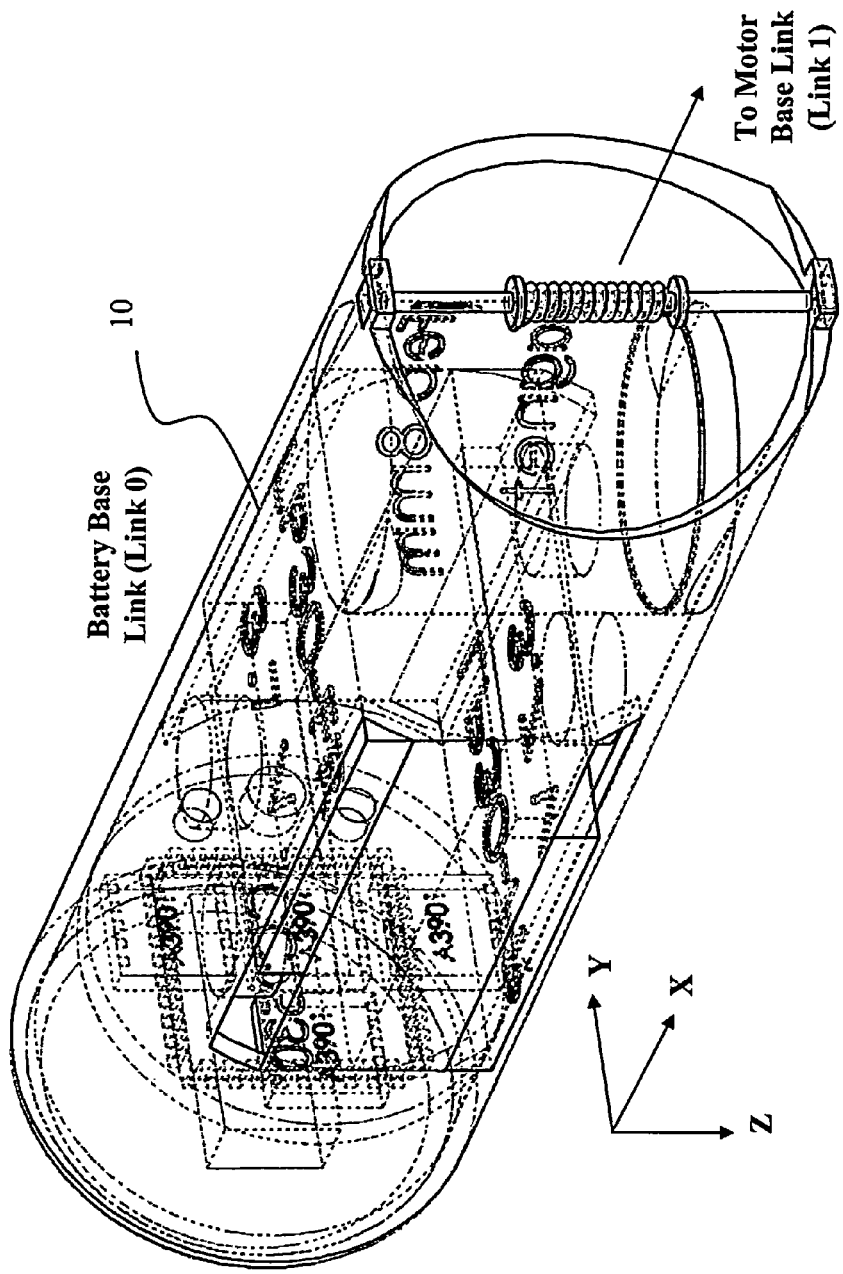
FIG. 12 is a CAD rendering of the battery base link (link 0) as viewed from an isometric projection with hidden lines. All components that are part of only this link (i.e. not shared by another link such as the case with certain transmission cables) are included, the neighboring links are specified, and the global coordinate axis is shown.
Figure 13:
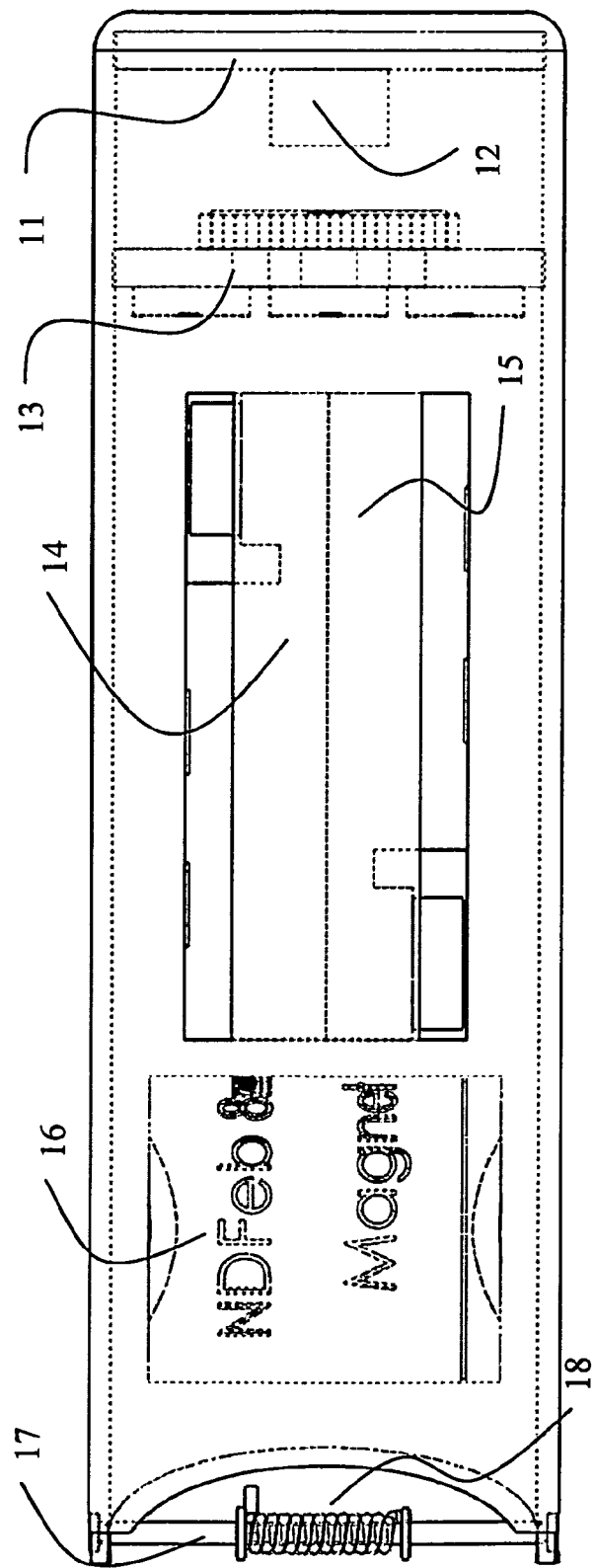
FIG. 13 is a CAD rendering of the battery base link (link 0) as viewed from the left side plane with hidden lines.
Figure 14:
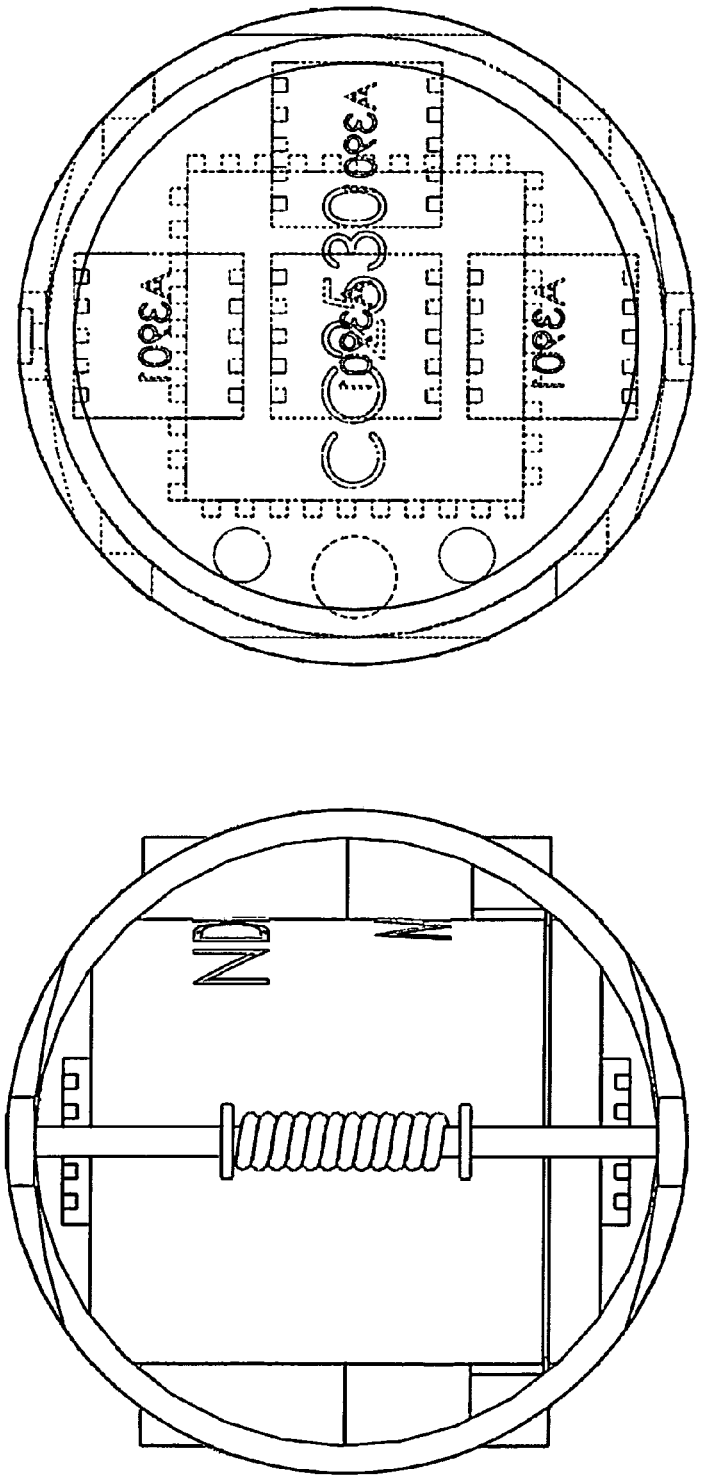
FIG. 14 is a CAD rendering of the battery base link (link 0) as viewed from the front plane without hidden lines and the back plane with partial hidden lines (only for showing the printed circuit board with the CC2530 and motor drivers).

Referring to FIGS. 12-14, the battery base link (link 0) 10 contains several components as well as open space for accommodating electrical wires. The first major element is a magnetic docking interface consisting of a cylindrical neodymium iron boron (NdFeB) permanent magnet 16 with a thickness and diameter of 8 mm. NdFeB magnets are rare-earth types and are the strongest permanent magnets. This magnet provides an axially directed magnetic force that is attracted by another magnet located external to the patient and fixed to a positioning manipulator's end effector. The force must be strong enough to act through the entire abdominal wall. This is the primary magnet used for docking, and the coupling force that results from this magnet and those embedded in the adjacent motor base link 20 has been verified to be sufficient for opposing the force and moment due to gravity on a suspended robotic module. If desired, this magnet can be replaced with a larger and stronger 9 mm thickness/diameter version without significantly altering any aspect of the design. It is necessary to shield and focus this magnet to prevent unintentional coupling with nearby magnets (e.g. those in neighboring robotic modules) and damage to on-board electronics.

The battery base link then includes two 3.7 V lithium-ion (Li-ion) polymer batteries 14,15 consisting of 30 mAh LP30-FR Bahoma cells. Rechargeable Li-ion polymer batteries are the preferred choice for an on-board power source due to the flexibility they offer, excellent charge density, and variety of shapes that are possible. These ultra-light batteries (1.16 g each) provide 60 mAh combined and considering that two 20 mAh LP20-FR Bahoma cells are also installed in link 6 90, a total of 100 mAh is available. Depending on the specific application, or the need to operate for an extended period of time, either higher power density batteries may be selected if available, or alternatively, a cable may be included for using a power source external to the module.

Towards the end of the battery base link, a circular printed circuit board (PCB) 13 with a diameter of 11 mm is provided that contains the Texas Instruments CC2530 system-on-chip (SoC) IEEE 802.15.4 compliant RF transceiver with a 8051 microcontroller core. This PCB is mainly used for managing the two motors located at the adjacent motor base link 20. The CC2530 SoC was selected due to its small form factor, ultra-low power consumption, and transceiver tailored for ZigBee (based on IEEE 802.15.4) communication. Up to four motor drivers may be included on the side opposite to the CC2530, and in the present embodiment the Allegro Microsystems A3901 drivers are used. Holes are formed in the PCB for routing wires. The robotic module is wirelessly teleoperated, where commands from a surgeon that have been processed by a computer external to the patient are wirelessly transmitted to antennas and transceivers installed in the robotic module. As such, the CC2530 wireless transceiver must be accompanied by an antenna. In this link, a CC2530 compliant Fractus Compact Reach Xtend chip antenna 12 connected to a PCB 11 is used for physically receiving wireless signals and then sending them to the CC2530 PCB 13.

Figure 15:
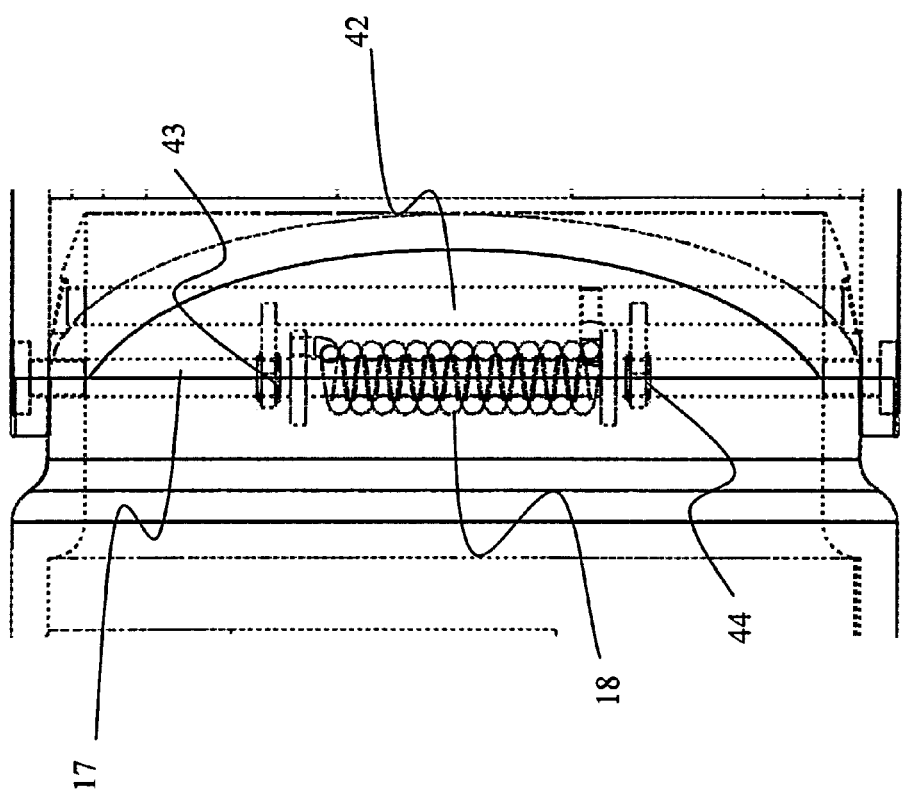
FIG. 15 is a CAD rendering of the spring damper mechanism that connects the battery base link (link 0) with the motor base link (link 1) as viewed from the left side plane with hidden lines. Components that are a part of this device are shown and numbered.

The final major component of the battery base link is a spring-damper mechanism that joins this link with the motor base link 20. Referring to FIG. 15, a shaft 17 rigidly fixed to the battery base link has one end of a torsion spring 18 connected to it. The other end of the spring is connected to a shaft 42 fixed to the motor base link. Two ring-shaped damping components 43,44 are then located on the extended portion of the shaft 42 at the area that is in contact with the shaft 17. The purpose of the spring is to provide a restoring force that favors the links to be parallel to one another. The damper components are included to damp the oscillations that occur from the spring. Together, the spring and dampers govern the relative motion at the joint bridging the two base links (link 0 and link 1) which was previously referred to as passive yaw DOF0. It is intended that motions are allowed during module overtube insertion, but once the module is docked, this DOF is suppressed such that the two links are forced to be parallel.

Figure 16:
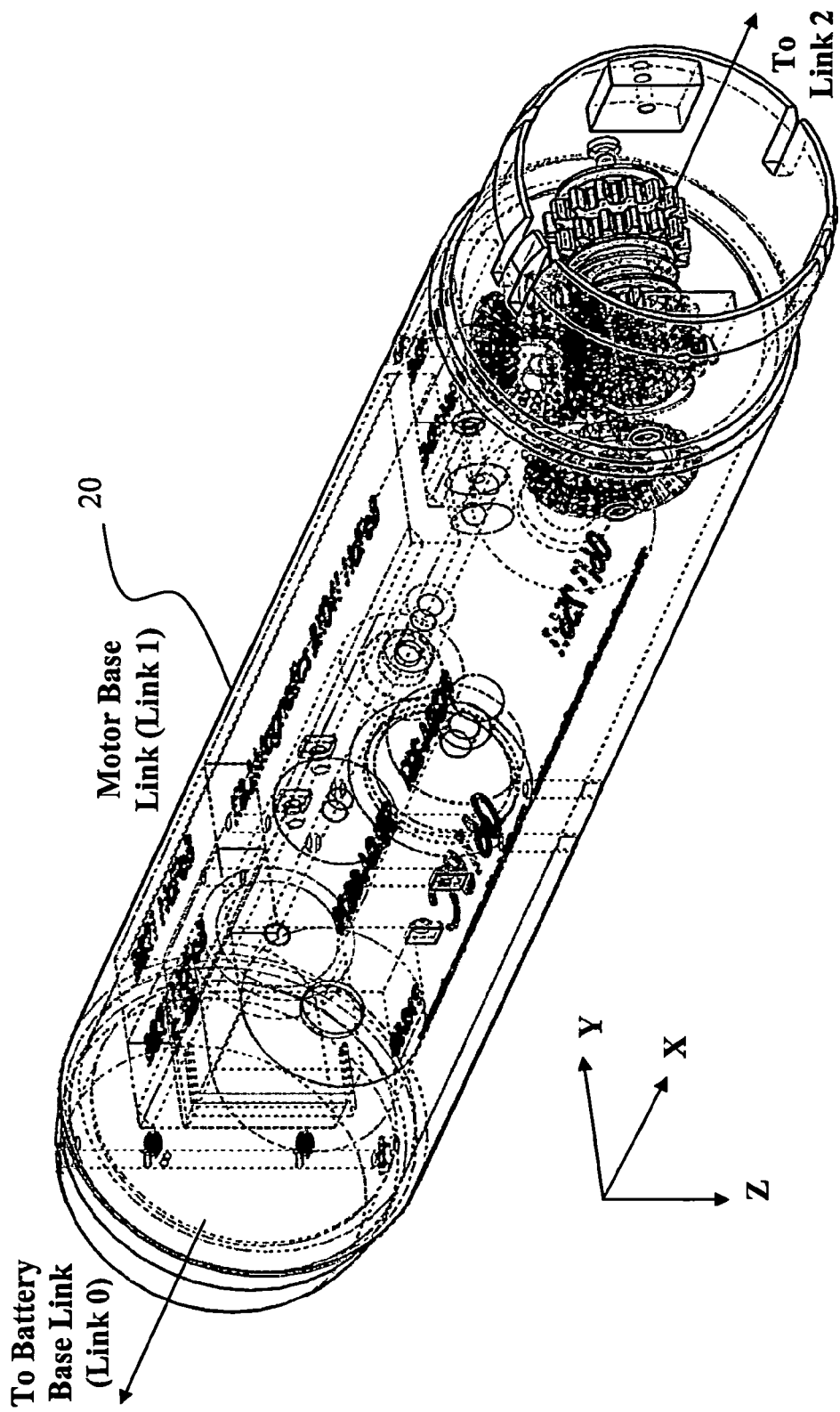
FIG. 16 is a CAD rendering of the motor base link (link 1) as viewed from an isometric projection with hidden lines. All components that are part of only this link are included, the neighboring links are specified, and the global coordinate axis is shown.
Figure 17:
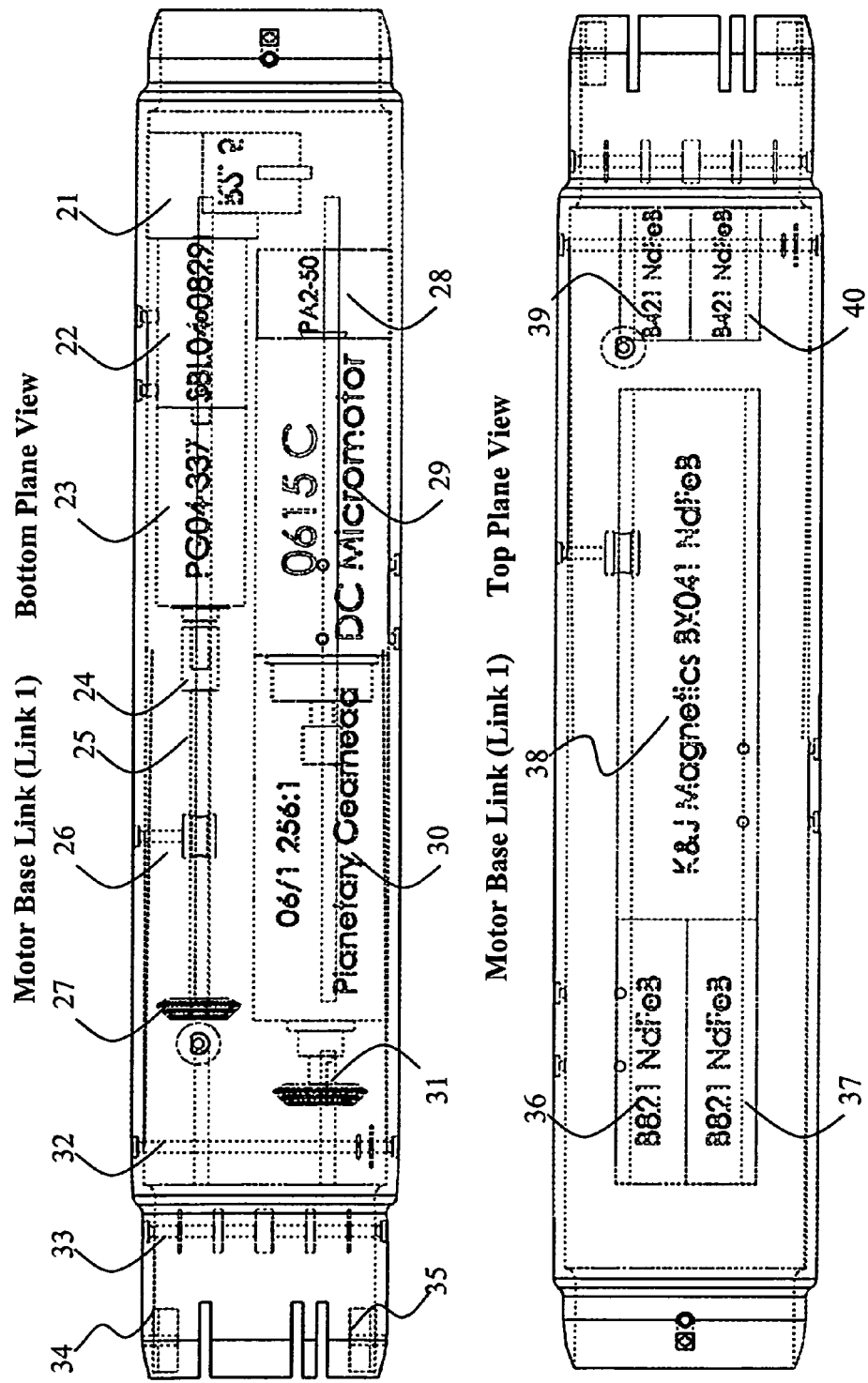
FIG. 17 is a CAD rendering of the motor base link (link 1) as viewed from the bottom plane with partial hidden lines (magnets not shown) and the top plane with partial hidden lines (motors not shown). Internal components are numbered. For better clarity of presentation, the following types of components are not shown: (a) free pulleys; (b) transmission cables; (c) non-motor gears; and (d) moving components of the transmission selection mechanism. Omission of the (a)-(d) components (which are instead presented in FIGS. 31-37) is also followed in FIGS. 18, 20, 22, 24, and 26.
Figure 18:
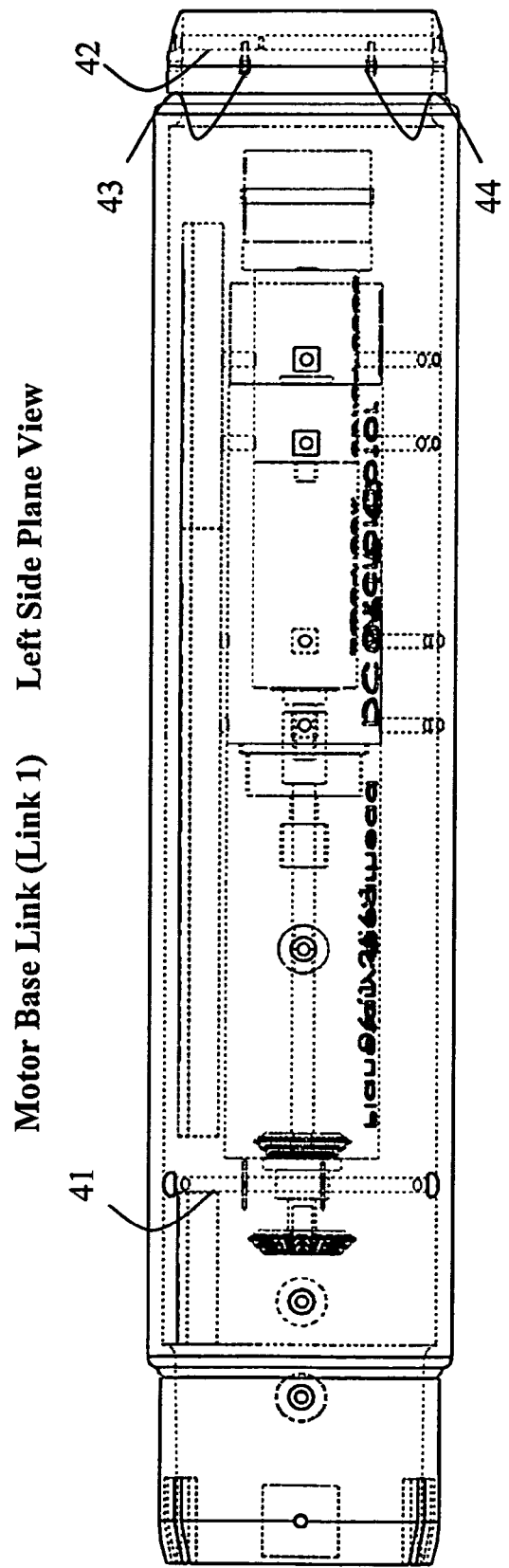
FIG. 18 is a CAD rendering of the motor base link (link 1) as viewed from the left side plane with hidden lines. Internal components are numbered.

Referring to FIGS. 16-18, the motor base link (link 1) 20 contains two DC geared micro-motors which together handle actuation of pitch DOF2, pitch DOF3, pitch DOF4, and yaw DOF5. For transmission selection (i.e. selecting which degree of freedom to actuate), a servo combination consisting of a 4 mm diameter Namiki SBL04-0829 motor 22 with a 337:1 reduction ratio PG04-337 gearhead 23 and a magnetic encoder 21 for precise feedback is used. This setup contributes only 1.53 g but has a low stall torque of 5.7 mNm. For reaching the transmission selection mechanism (discussed later) an extended rod 25 stabilized by a perpendicular shaft 26 is connected to the motor shaft by a coupling 24. A bevel gear 27 is then provided at the end of the extended rod for changing the axis of rotation by 90°. Next, for transmission actuation (i.e. actuating the degrees of freedom), a higher torque servo combination consisting of the 6 mm diameter MicroMo 0615C coreless DC motor 29 with a 256:1 reduction ratio planetary gearhead 30 and an optical encoder PA2-50 28 for precise feedback is used. This setup contributes 7 g but also has a higher stall torque of 33.8 mNm. A bevel gear 31 is provided at the end of the motor shaft for a 90° change in the axis of rotation.

The motor base link also contains a magnetic docking interface comprised of several rectangular NdFeB permanent magnets 36,37,38,39,40 with thru thickness magnetization. Although covering a wide area, these magnets have a relatively small thickness, and therefore do not generate the substantial magnetic forces that are possible with an 8 or 9 mm thick version. The purposes of these magnets are to not only provide an additional coupling force, but also interact with a second external magnet for suppressing the passive pitch yaw DOF0. Referring to FIG. 18, the elements 42,43,44 of the spring damper mechanism that characterizes this passive degree of freedom are included at the end of the link. With two internal magnetic interfaces (one in link 0 and another in link 1) located at a distance from one another and also two external magnets fixed to the end effector of a rigid positioning manipulator, yaw rotations (yaw DOF1) of the entire device can be performed in addition to docking and gross translations. It is thus evident that among the six major rotation degrees of freedom, yaw DOF1 is the only one that is not actuated by an onboard micro-motor.

Another major component located in the motor base link is the transmission selection mechanism which consists of a slider-crank, several pulleys, shafts, cables, and gears (both bevel and spur types). This mechanism forms the beginning of a remote cable-drive transmission system that is then propagated up to link 5. For facilitating the discussion and providing clear pictures that are easy to analyze, only the shafts 32, 33, and 41 are included in FIGS. 17-18. A discussion of the selection mechanism and transmission system is thus deferred to future paragraphs that refer to FIGS. 30-37.

A concern associated with the idea of transmission selection is that only one degree of freedom among pitch DOF2, pitch DOF3, pitch DOF4, and yaw DOF5 may be actuated at any given time. If unaccounted for, rotations will occur at non-actuated joints due to the gravitational force as well as because of the coupled nature of the system when actuating other joints. This problem is addressed by using damping elements (material with a high static friction) at each link joint to prevent such motions. The material and dimensions must be carefully chosen such that without any rotating motors, the robotic module can maintain a position even under the influence of gravity. The motor must then counteract the frictional force imposed by the damping material for imparting rotation at a given joint. These damping mechanisms contain a hole for which a shaft located at one link goes through and a curved outer surface that is fixed to the inner cylindrical wall of the adjacent link. The dampers in the motor base link are indicated as 34 and 35 (where the curved surface is fixed to this link).

Figure 19:
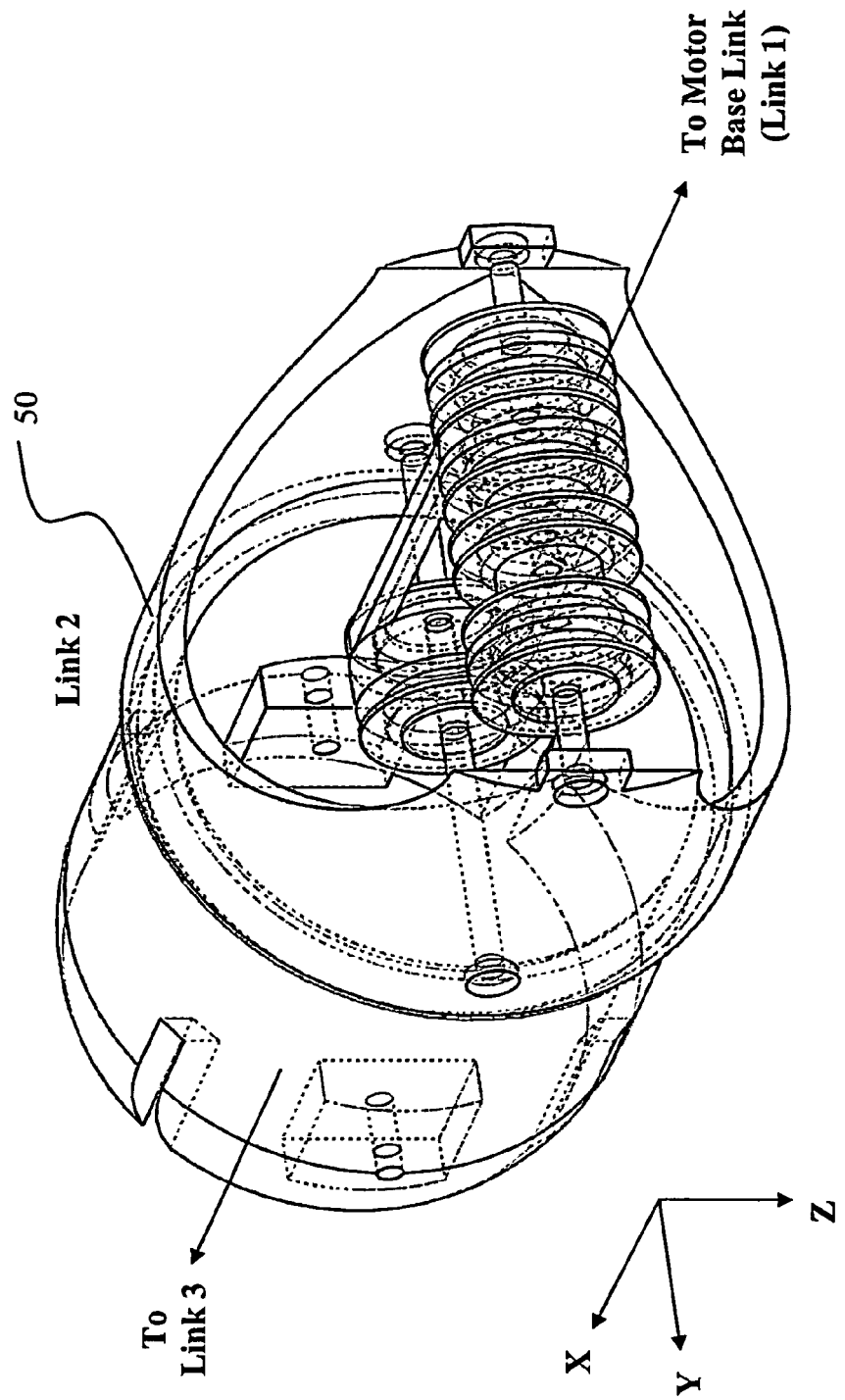
FIG. 19 is a CAD rendering of link 2 as viewed from an isometric projection with hidden lines. All components that are part of only this link are included, the neighboring links are specified, and the global coordinate axis is shown.

Referring to FIGS. 19-20, link 2 50 contains several pulleys and shafts for propagating the cable-drive transmission system. For ease of analysis, all elements that are only a part of this link (i.e. not shared by the adjacent link such as the case with certain cables) are shown in FIG. 19, and only those that do not move with respect to the link are provided in FIG. 20. Components that are numbered include two shafts 51,52 and a pulley 55 that is rigidly fixed to shaft 51 and does not rotate with respect to the cylindrical body. This type of pulley is referred to as a "fixed pulley", since once it rotates the cylindrical link that it is fixed to rotates as well. This is in contrast to "free pulleys" (shown in FIG. 19 but not FIG. 20) which rotate freely about the link they are a part of and are used for simply propagating a given transmission through the robotic module. These types of pulleys as well as their cables are illustrated and numbered in FIGS. 31-37 (referred by future paragraphs discussing the transmission system). Finally, the damping components 53,54 are included in FIG. 20.

Figure 21:
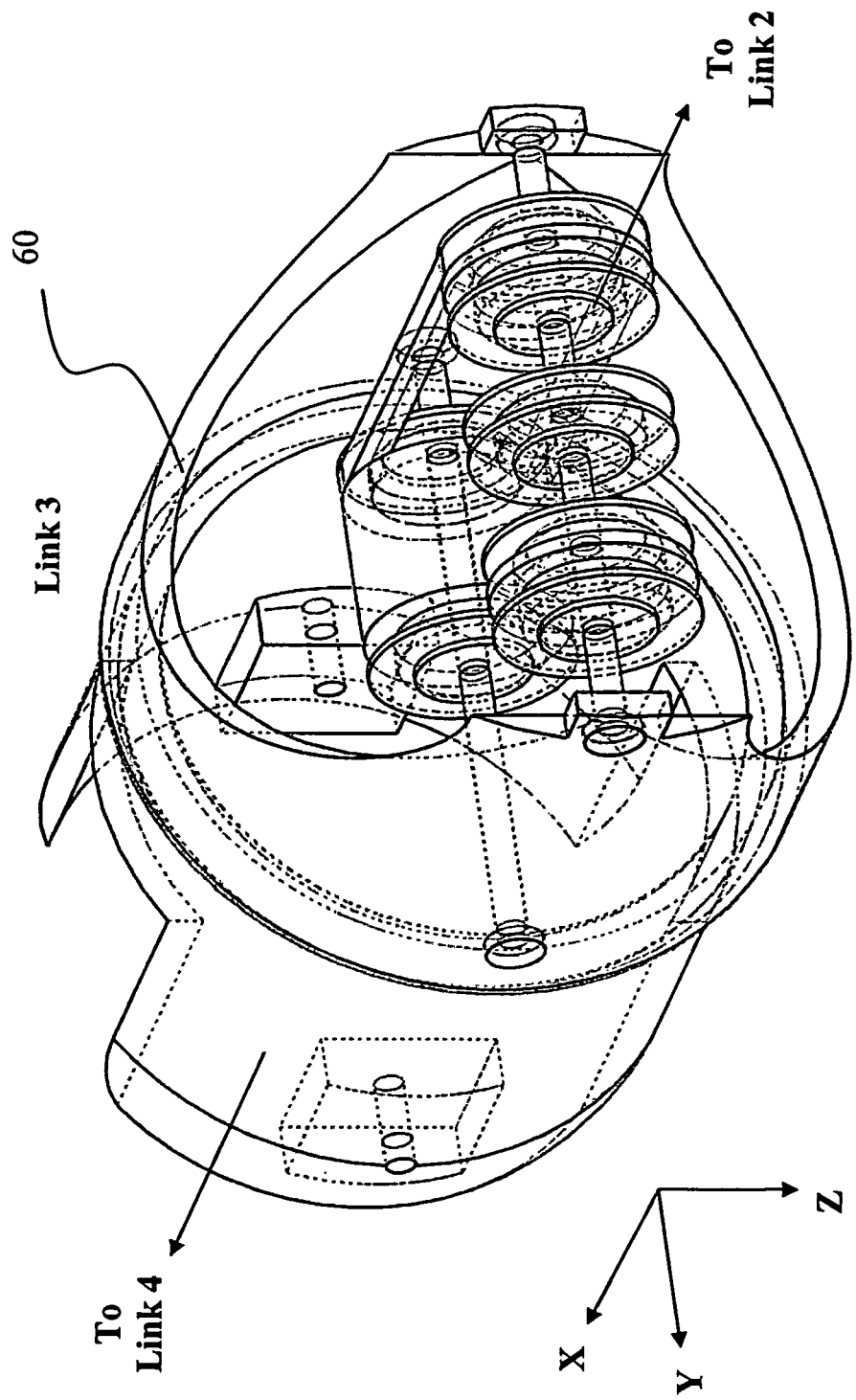
FIG. 21 is a CAD rendering of link 3 as viewed from an isometric projection with hidden lines. All components that are part of only this link are included, the neighboring links are specified, and the global coordinate axis is shown.

Referring to FIGS. 21-22, link 3 60 contains several pulleys and shafts for propagating the cable-drive transmission system. All elements that are only a part of this link are shown in FIG. 21, and only those that do not move with respect to the link are provided in FIG. 22. Components that are numbered in FIG. 22 include two shafts 61,62, a fixed pulley 65, and two damping components 63,64.

Figure 23:
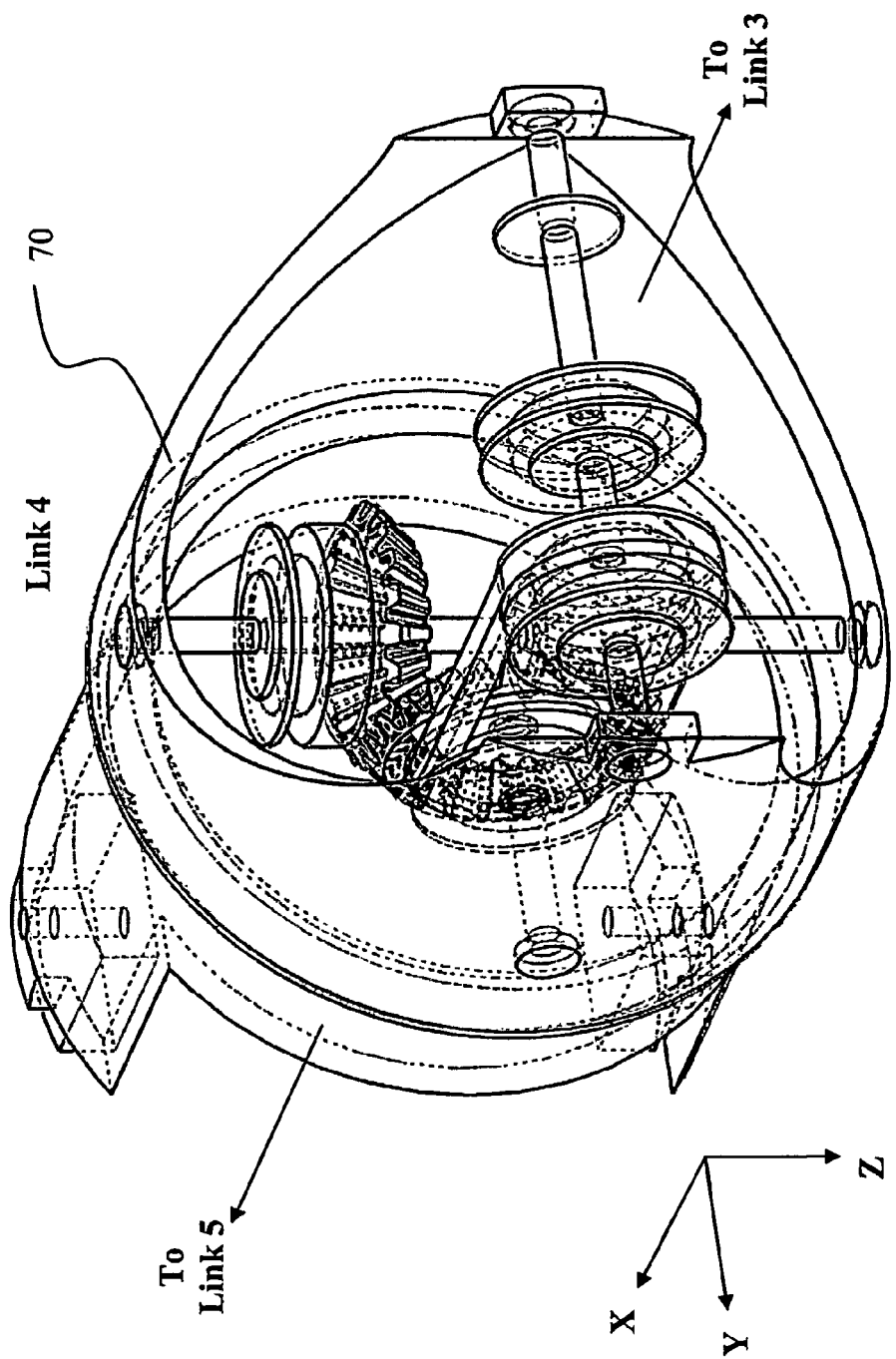
FIG. 23 is a CAD rendering of link 4 as viewed from an isometric projection with hidden lines. All components that are part of only this link are included, the neighboring links are specified, and the global coordinate axis is shown.

Referring to FIGS. 23-24, link 4 70 contains several pulleys, shafts, and bevel gears for propagating the cable-drive transmission system. All elements that are only a part link of this link are shown in FIG. 23, and only those that do not move with respect to the link are provided in FIG. 24. Components that are numbered in FIG. 24 include three shafts 71,72,76, a fixed pulley 73, and two damping components 74,75.

Figure 25:
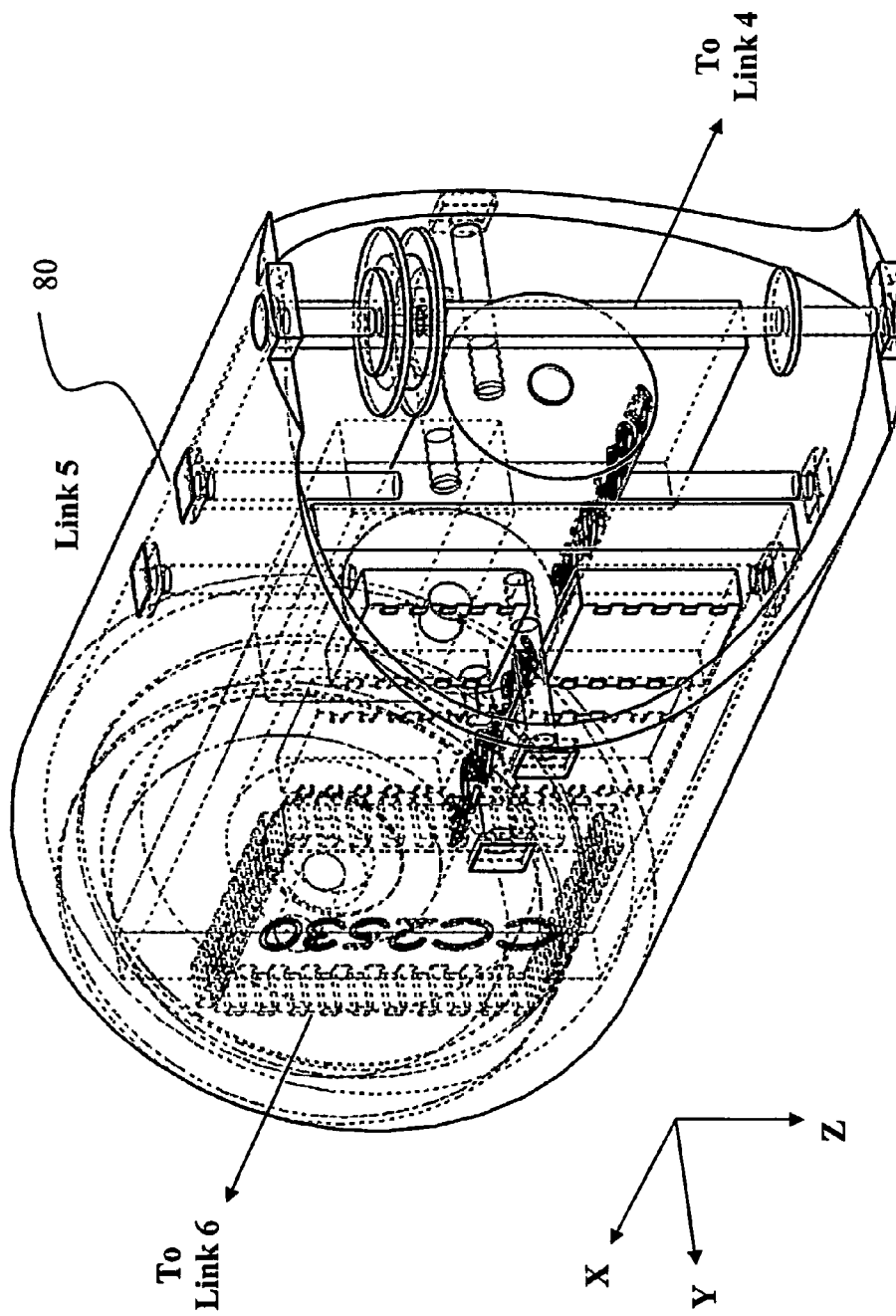
FIG. 25 is a CAD rendering of link 5 as viewed from an isometric projection with hidden lines. All components that are part of only this link are included, the neighboring links are specified, and the global coordinate axis is shown.
Figure 26:
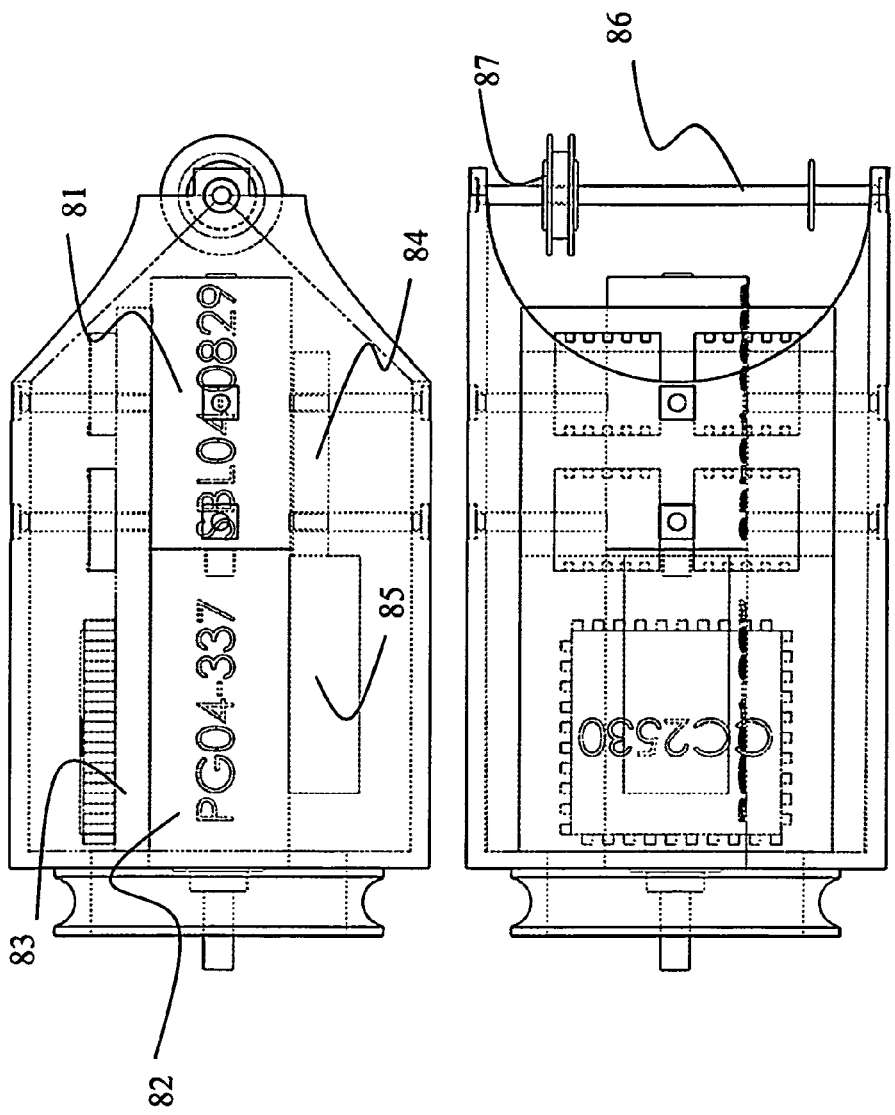
FIG. 26 is a CAD rendering of link 5 as viewed from the bottom and left side planes with hidden lines. Internal components are numbered.

Referring to FIGS. 25-26, link 5 80 contains the 4 mm diameter Namiki SBL04-0829 motor 81 with a 337:1 reduction ratio PG04-337 gearhead 82. This motor is used for directly actuating the roll DOF6. Since this degree of freedom is met with less resistance forces that the others, a lower torque motor is sufficient. The magnetic encoder is not included in the current design as the motor provides sensor outputs which serve as an indicator of the angular displacement. However, if higher accuracy position feedback is desired, the only modification necessary to incorporate the encoder would be to slightly extend the link in length. For managing this motor as well as the motor that actuates the end effector of the adjacent link 6 90, link 5 contains a printed circuit board 83 with the CC2530 system-on-chip microcontroller/wireless transceiver and up to four A3901 motor drivers. For receiving signals from the remote computer, the CC2530 wireless transceiver must be accompanied by an antenna. In this link, a CC2530 compliant Fractus Compact Reach Xtend chip antenna 85 connected to another PCB 84 is used for receiving wireless signals and then sending them to the PCB 83. In addition, feedback and sensor status/signals can be sent back to the remote computer. Link 5 contains a shaft 86 and fixed pulley 87 as the final elements of the transmission system. Lastly, an inner race of a ball-bearing track is included at the motor shaft side of the link (at the left in FIG. 26).

Figure 27:
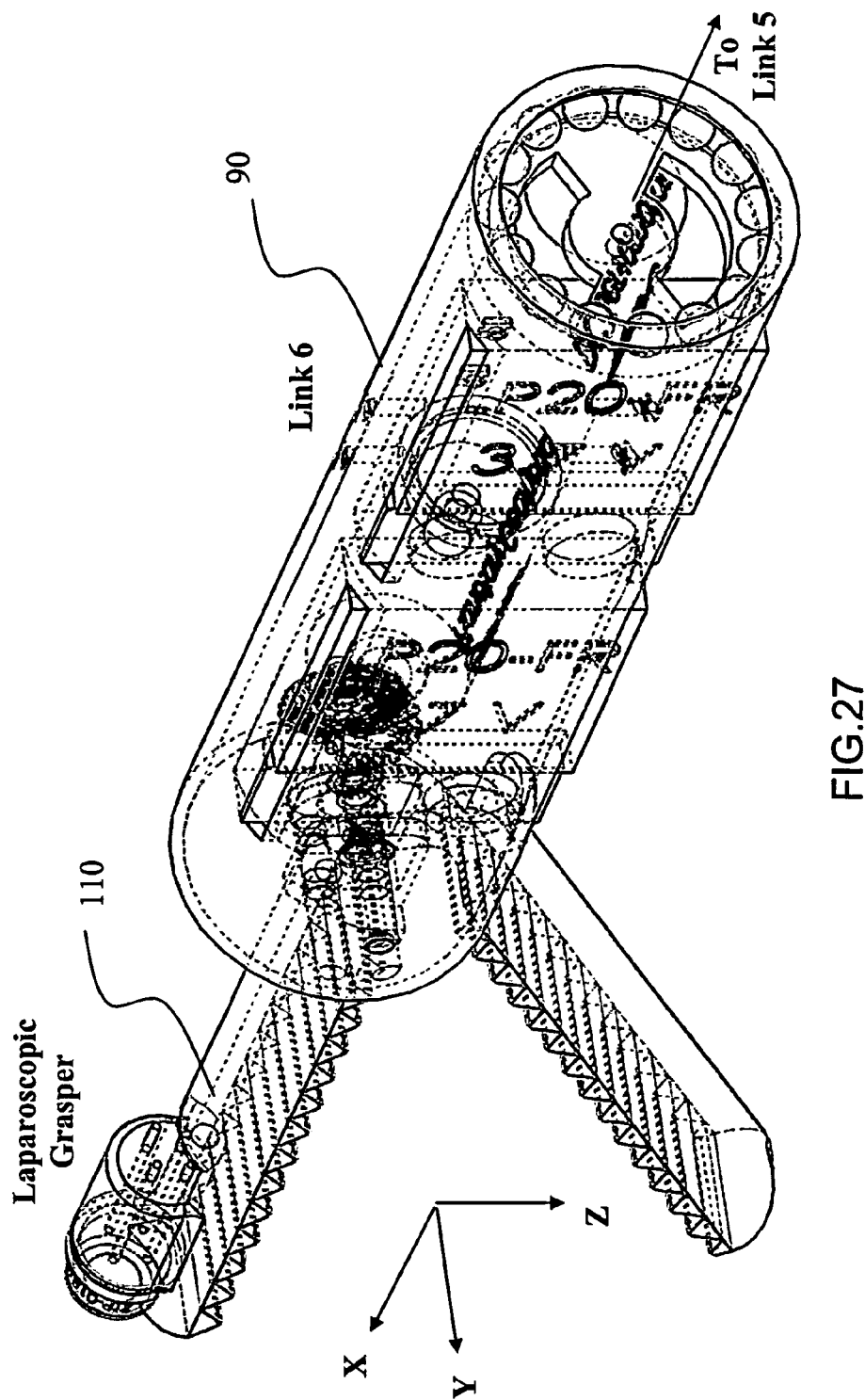
FIG. 27 is a CAD rendering of link 6 with a laparoscopic grasper viewed from an isometric projection with hidden lines. All components that are part of only this link are included, the neighboring links are specified, and the global coordinate axis is shown.
Figure 28:
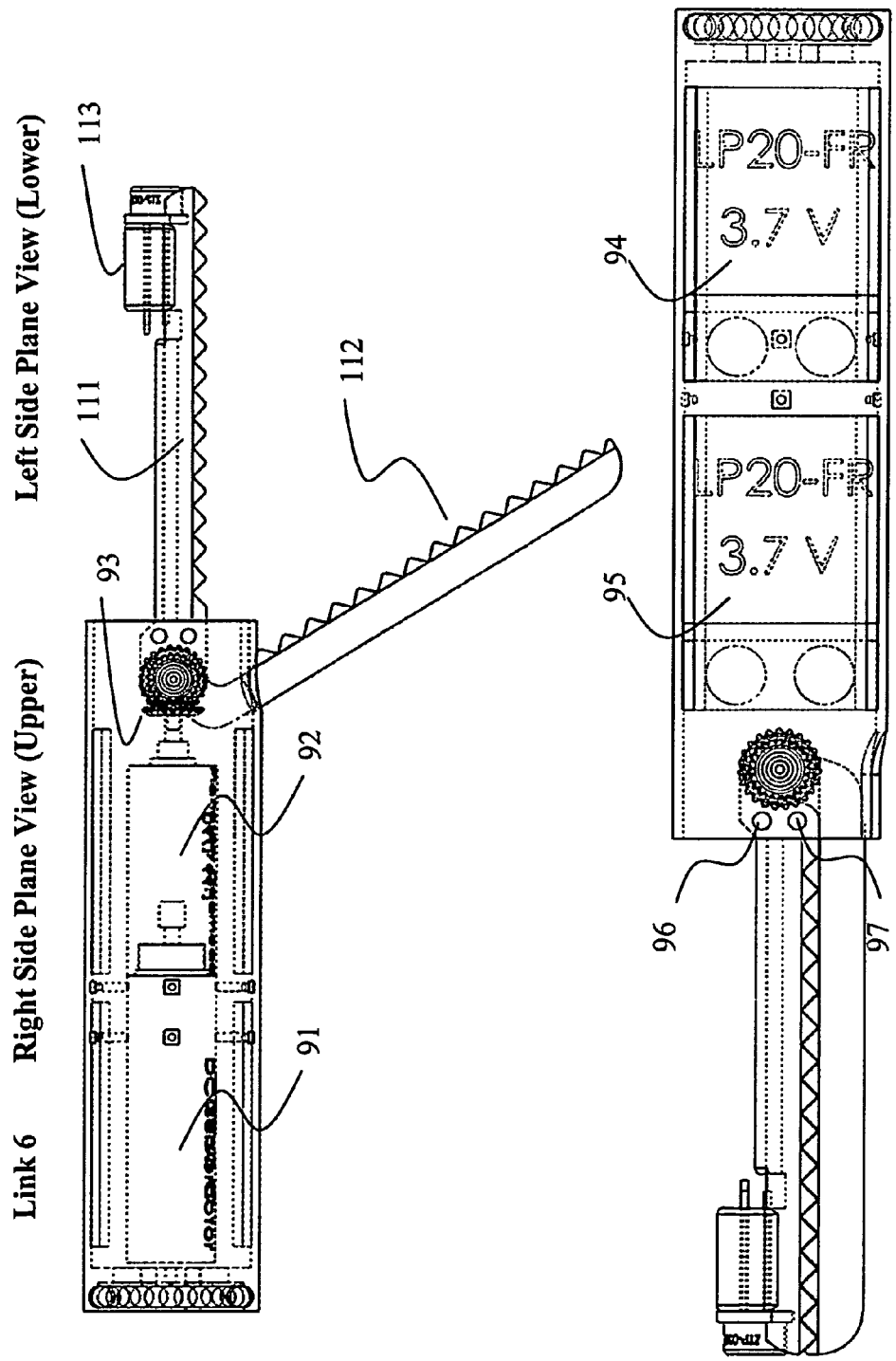
FIG. 28 is a CAD rendering of link 6 with a laparoscopic grasper as viewed from the right side plane with partial hidden lines (batteries not shown) and the left side plane with partial hidden lines (motor not shown). Internal components are numbered.

Referring to FIGS. 27-29, link 6 90 consists of several internal components and is fitted with a custom laparoscopic grasper 110 as an end effector. For facilitating the roll DOF6, the outer race of a ball-bearing track with spherical bearings 100 is included. Two ultra-light (0.95 g each) 3.7 V Li-ion polymer batteries 94,95 consisting of 20 mAH LP20-FR Bahoma cells are included, thus providing a total of 100 mAh for the robotic module. For actuating the laparoscopic grasper, the MicroMo 0620C brushless DC servomotor 91 with a 64:1 reduction ratio planetary gearhead 92 is used. This servomotor contains sensor signals for feedback and therefore a separate encoder is not necessary. The setup contributes 5.9 g and has a stall torque of 32.7 mNm. A bevel gear 93 is provided at the end of the shaft which rotates another bevel gear 98 for changing the axis of rotation by 90°. This bevel gear is connected to a hollowed out shaft which rotates about the fixed shaft 99. Since the hallowed out shaft is connected to the lower blade of the grasper 112, rotation of bevel gear 98 causes rotation of the grasper blade 112.

One of the motivating design considerations for the robotic modules is that they can be installed with a variety of laparoscopic tools, and thereby realize different surgical functionalities. As such, a custom laparoscopic grasper 110 is provided in the present embodiment as an example of one possible tool. The grasper presented here is similar to straight, single-action grasping forceps with several triangular teeth. The straight classification refers to the geometry of the blade, and it is single action as one blade 112 moves during actuation, with the other 111 remaining stationary. As evident from FIG. 28, when the grasper is closed, no parts extend beyond the 12 mm diameter of the robotic module, thereby not posing a problem for overtube transport. The upper blade 111 is fixed to link 6 via two rigid shafts denoted as 96,97. The bevel gear 98 is used to rotate the lower blade 112 about shaft 99. This is just one possibility for interfacing a laparoscopic type grasper with link 6, and other methods can be used as well, depending on the particular tool and if the design must instead accommodate a commercial-off-the-shelf version. The final remaining element is a non-invasive infrared (IR) temperature sensor 113 by Thermometrics, ZTP-015 included at the end of the upper blade. This sensor can be used to construct an infrared image depicting the temperature of surrounding tissue and organs. The signals from this sensor are sent by electrical wires to the PCB 83 and then to the chip antenna 85 located in link 5. Although the embodiment of the present invention includes only this sensor, other types such as an imaging camera can certainly be integrated. The choice of sensor suites depends on the requirements of the surgical procedure to be carried out.

The remote cable-drive transmission system is a key component that was designed for alleviating several concerns associated with using a six DOF manipulator for performing tasks of clinical relevance. The standard method of actuating joints in a robotic manipulator is to have a motor directly driving a single joint, referred to as "direct actuation". Considering the current manipulator kinematic structure, with direct actuation a geared micro-motor would be required at each link, resulting in a total of six motors (for pitch DOF2, pitch DOF3, pitch DOF4, yaw DOF5, roll DOF6, and laparoscopic actuation). This integration of all these motors would result in long link lengths and additional module weight. The increased length would limit clinical applicability and the heavier weight would necessitate the integration of higher torque motors (which in turn may result in even further length increases). Moreover, more printed circuit boards with microcontrollers and motor drivers would be necessary to handle all of these motors. For these reasons, a remote cable-drive transmission system has been designed which requires only four motors (two motors for pitch DOF2, pitch DOF3, pitch DOF4, and yaw DOF5, one motor for roll DOF6, and one motor for laparoscopic actuation). With this system, two of the motors can be embedded in the motor base link (link 1) which is fixed to the inner abdominal skin wall via magnetic coupling forces. This is beneficial as the masses of these motors would then not contribute to the moment due to gravity of links 2-6 that tends to rotate those links counterclockwise (referring to FIG. 4) at their joints. This has the advantage in that lower torque motors may be used for driving those links. Considering all of these reasons, a remote cable-drive transmission system has been realized as discussed in the following paragraphs.

Figure 30:
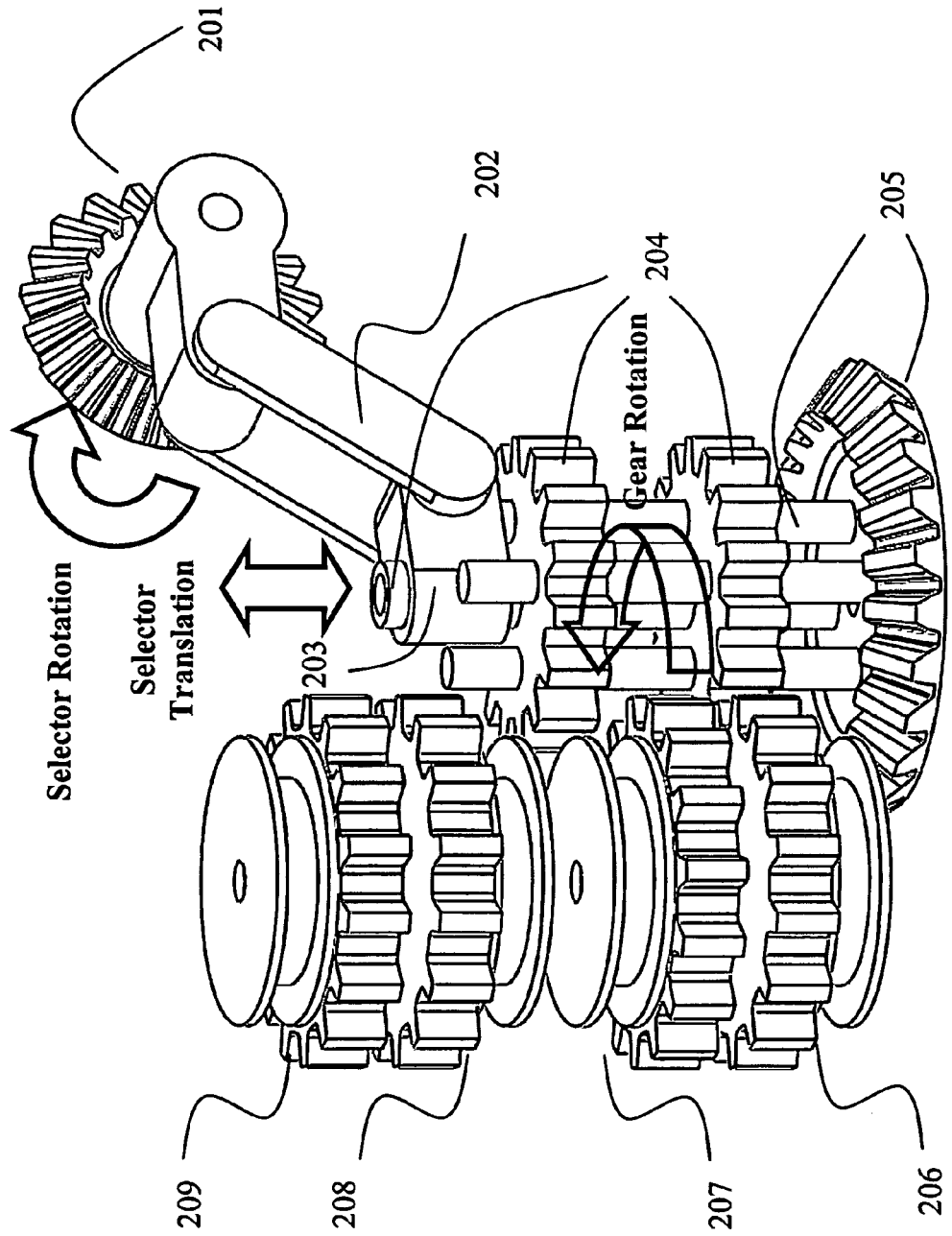
FIG. 30 is a CAD rendering of the transmission selection mechanism. Components that are a part of this device are shown and numbered.
Figure 31:
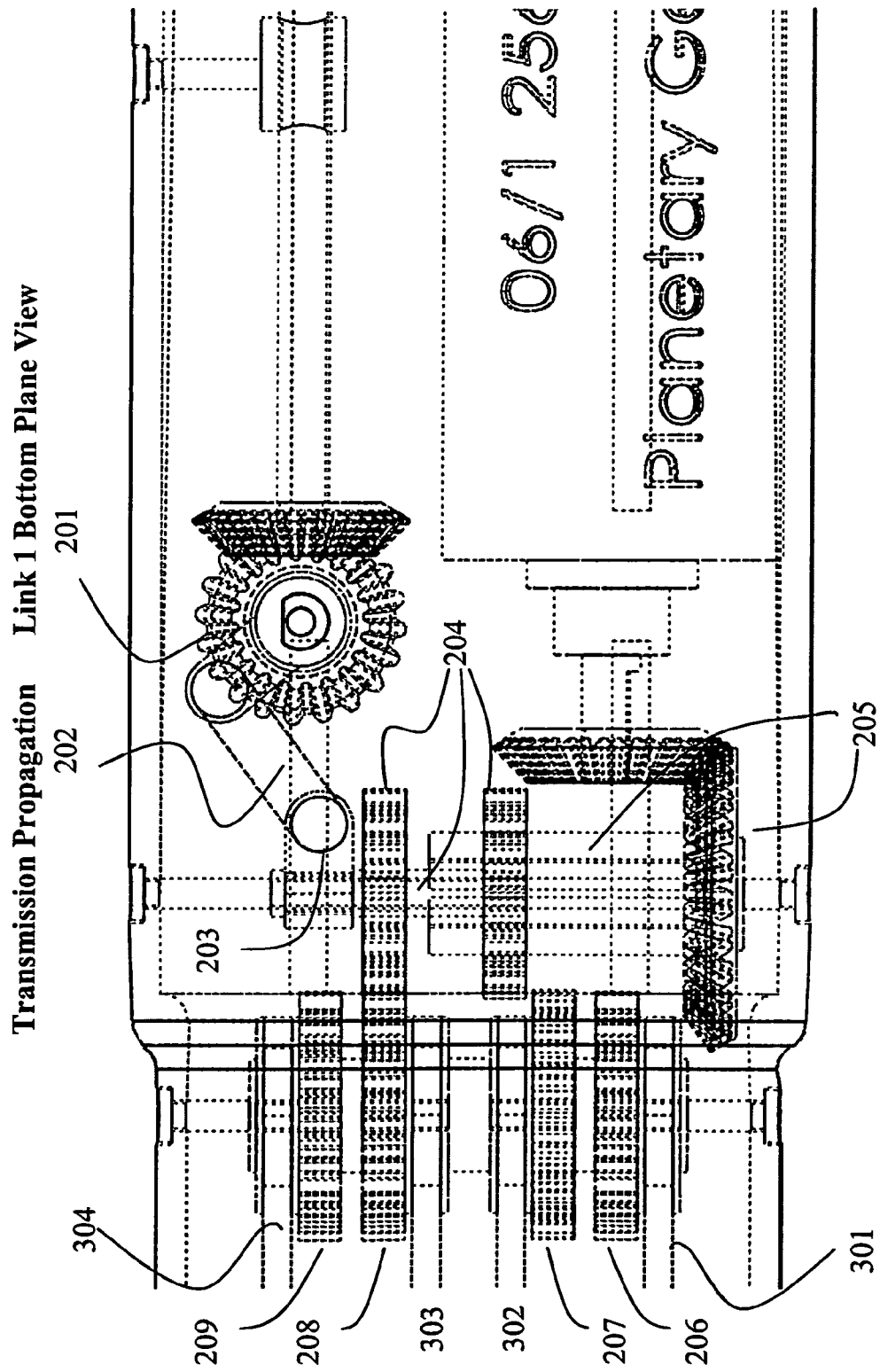
FIG. 31 is a CAD rendering of the cable-drive transmission system in the motor base link (link 1) as viewed from the bottom plane with partial hidden lines (magnets not shown). Components that comprise the transmission system are numbered.
Figure 35:
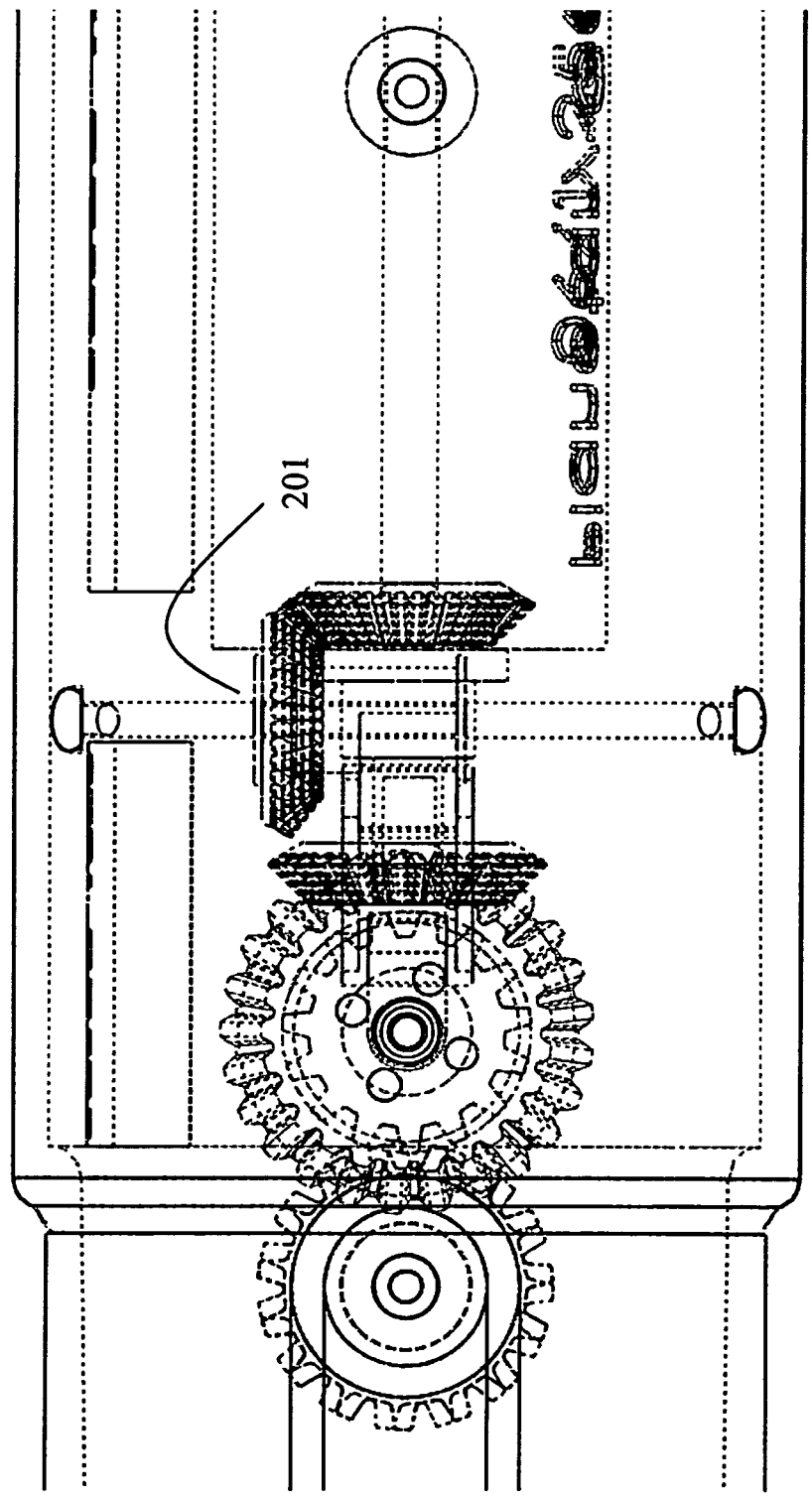
FIG. 35 is a CAD rendering of the cable-drive transmission system in the motor base link (link 1) as viewed from left side plane with hidden lines.

Referring to FIGS. 30, 31, and 35, a transmission selection mechanism is utilized for selecting the desired degree of freedom (among pitch DOF2, pitch DOF3, pitch DOF4, and yaw DOF5) to be actuated. The transmission selection servo motor combination 21,22,23 rotates bevel gear 27, which in turn rotates bevel gear 201 (altering the axis of rotation by 90°). Components 201,202,203,204 comprise a slider-crack mechanism that allows linear translation of the spur gears in 204 (referred to as the "sliding gears") about a shaft 32. This mechanism converts the rotation of 201 into a translation of 204 which then allows for selecting which gear among 206, 207,208,209 (referred to as the "transmission gears") to mesh with. In addition, the transmission actuation servo motor combination 28,29,30 rotates bevel gear 31, which in turn rotates bevel gear 205 (altering the axis of rotation by 90°). Several "forks" consisting of long cylindrical sections are fixed to bevel gear 205. These forks are concentrically aligned with holes in the sliding gears of 204, such that as bevel gear 205 rotates, the gears in 204 rotate as well. Therefore, the two sliding gears that comprise 204 are able to not only move linearly up and down the shaft 32, but are also free to rotate about that shaft as well. Two sliding gears are chosen for minimizing the distance required for translating, and it should be noted that these gears comprise a single component, and therefore rotate together. This is unlike the transmission gears which may rotate independently from one another about shaft 33. Accommodating both rotation and translation of these gears is possible as 204 may rotate inside 203, and 204 contains a slider bearing for moving along shaft 32. All the gears shown are carefully given separation distances such that only one gear on the sliding track meshes with only one transmission gear (among 206,207,208,209) at any given time. Therefore, only one transmission is active at once. The obvious limitation of this is that simultaneous actuation of these four degrees of freedom is not possible, slightly complicating the motor control algorithm. However, transitioning to different transmissions can occur quite rapidly as the distance required to move the sliding gears is minimal. The success of this mechanism relies on the gears 206,207,208,209 not rotating if not being actuated. Otherwise, the transmission gears may not be aligned with the sliding gears, and linear translation may be blocked. This would occur if a cylindrical link rotates without being actuated, which may occur due to the coupled nature of the manipulator when other links are moving and also due to forces from gravity. However, this issue was handled with the previously discussed damping components. Nonetheless, misalignment and inadvertent joint rotations still remain the highest risks of the robotic module design. Finally, rotation of the transmission gears 206,207,208,209 causes rotation of the pulleys fixed to these gears, and thus rotation of cables 301,302,303,304 respectively. Although not shown, a method other than friction must be employed such that a spinning pulley causes rotation of the cables (can be accomplished by aligned groves in the cables and pulleys).

Figure 32:
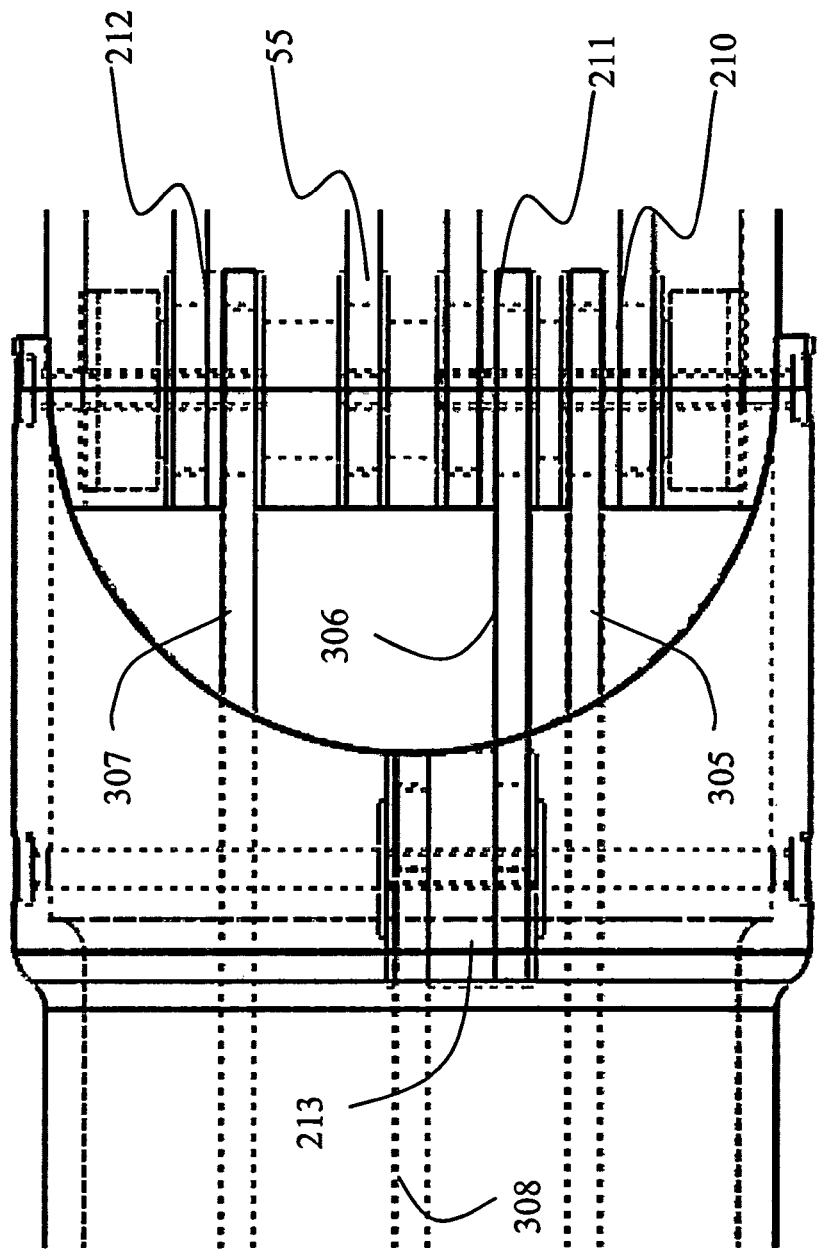
FIG. 32 is a CAD rendering of the cable-drive transmission system in link 2 as viewed from the bottom plane with hidden lines. Components that comprise the transmission system are numbered.
Figure 36:
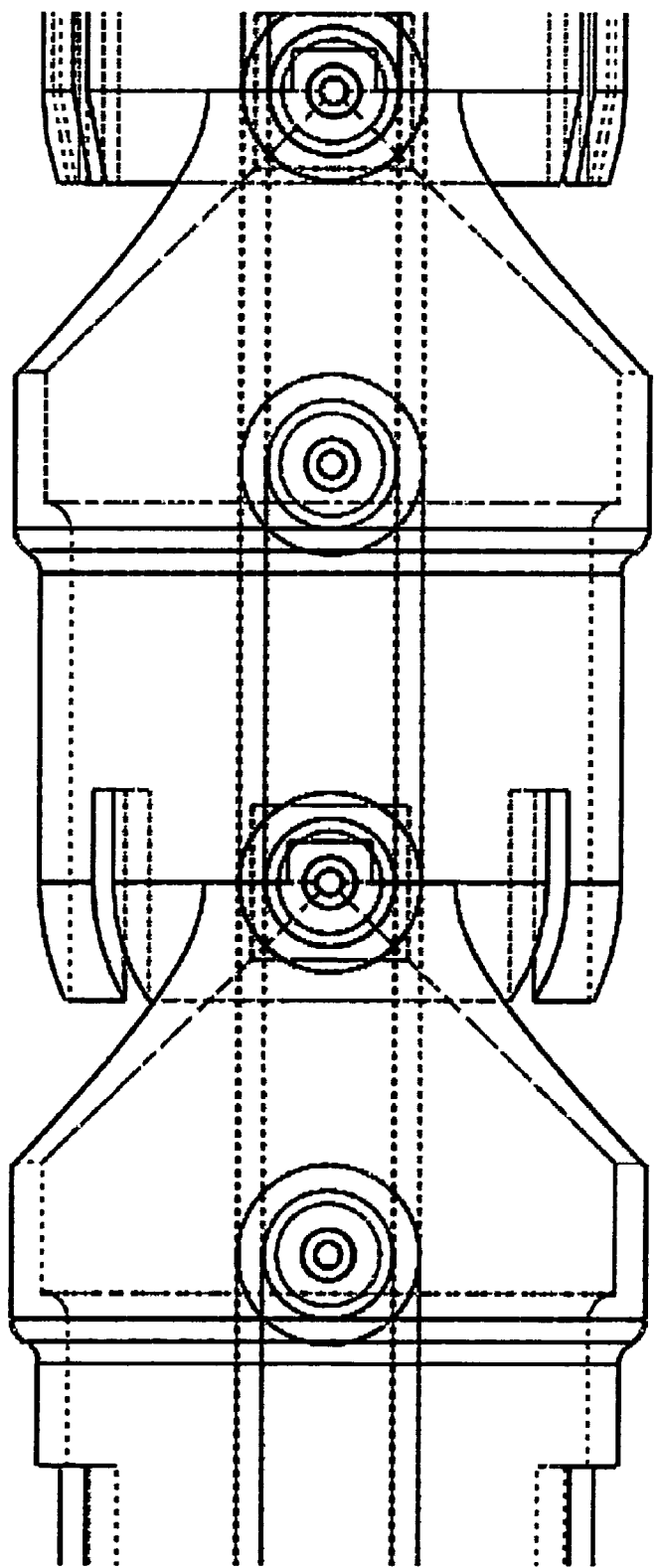
FIG. 36 is a CAD rendering of the cable-drive transmission system in link 2 and link 3 as viewed from left side plane with hidden lines.

Referring to FIG. 32 and FIG. 36, the transmission system continues through link 2. There, cable 301 (associated with the 206 transmission gear) rotates free pulley 210 which in turn rotates another cable 305. Cable 302 (associated with the 207 transmission gear) rotates free pulley 211, which in turn rotates another cable 306. Then, this cable rotates free pulley 213, which rotates cable 308. Next, cable 303 (associated with the 208 transmission gear) rotates fixed pulley 55 which causes rotation of link 2, and thus actuation of pitch DOF2. Finally, cable 304 (associated with the 209 transmission gear) rotates free pulley 212, which in turn rotates another cable 307.

Figure 33:
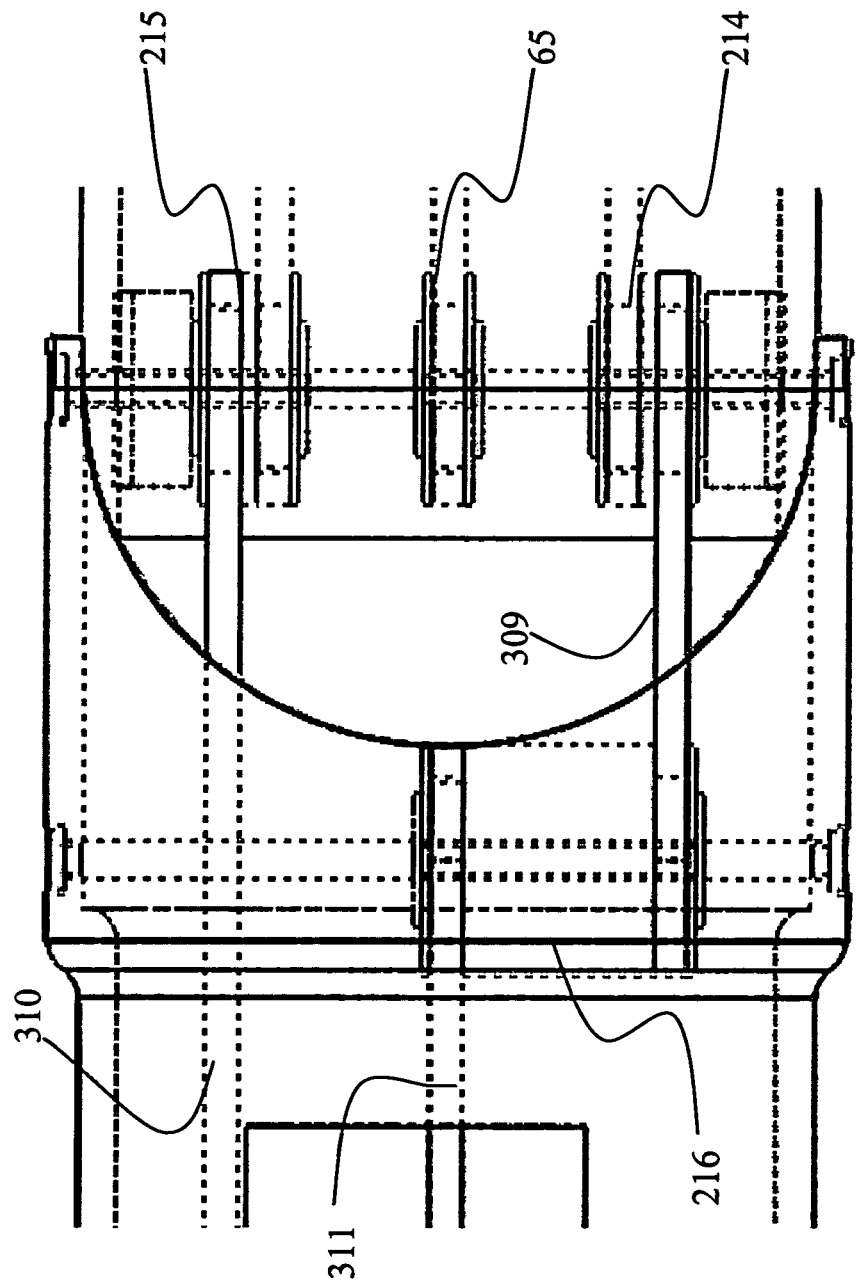
FIG. 33 is a CAD rendering of the cable-drive transmission system in link 3 as viewed from the bottom plane with hidden lines. Components that comprise the transmission system are numbered.

Referring to FIG. 33 and FIG. 36, the transmission system continues through link 3. There, cable 305 rotates free pulley 214, which in turn rotates another cable 309. Then, this cable rotates free pulley 216, which rotates cable 311. Next, cable 308 rotates fixed pulley 65 which causes rotation of link 3, and thus actuation of pitch DOF3. Finally, cable 307 rotates free pulley 215, which in turn rotates another cable 310.

Figure 34:
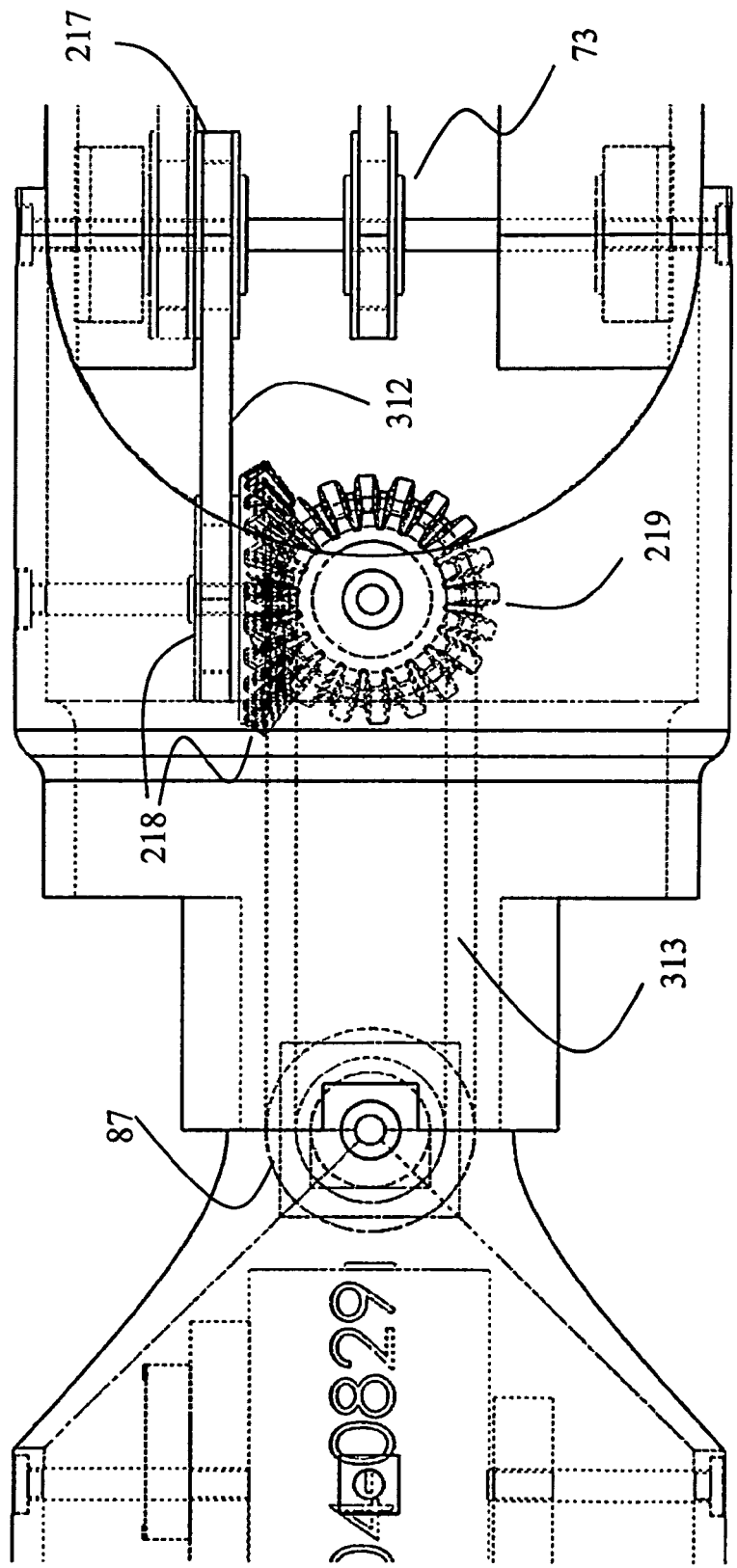
FIG. 34 is a CAD rendering of the cable-drive transmission system in link 4 as viewed from the bottom plane with hidden lines. Components that comprise the transmission system are numbered.
Figure 37:
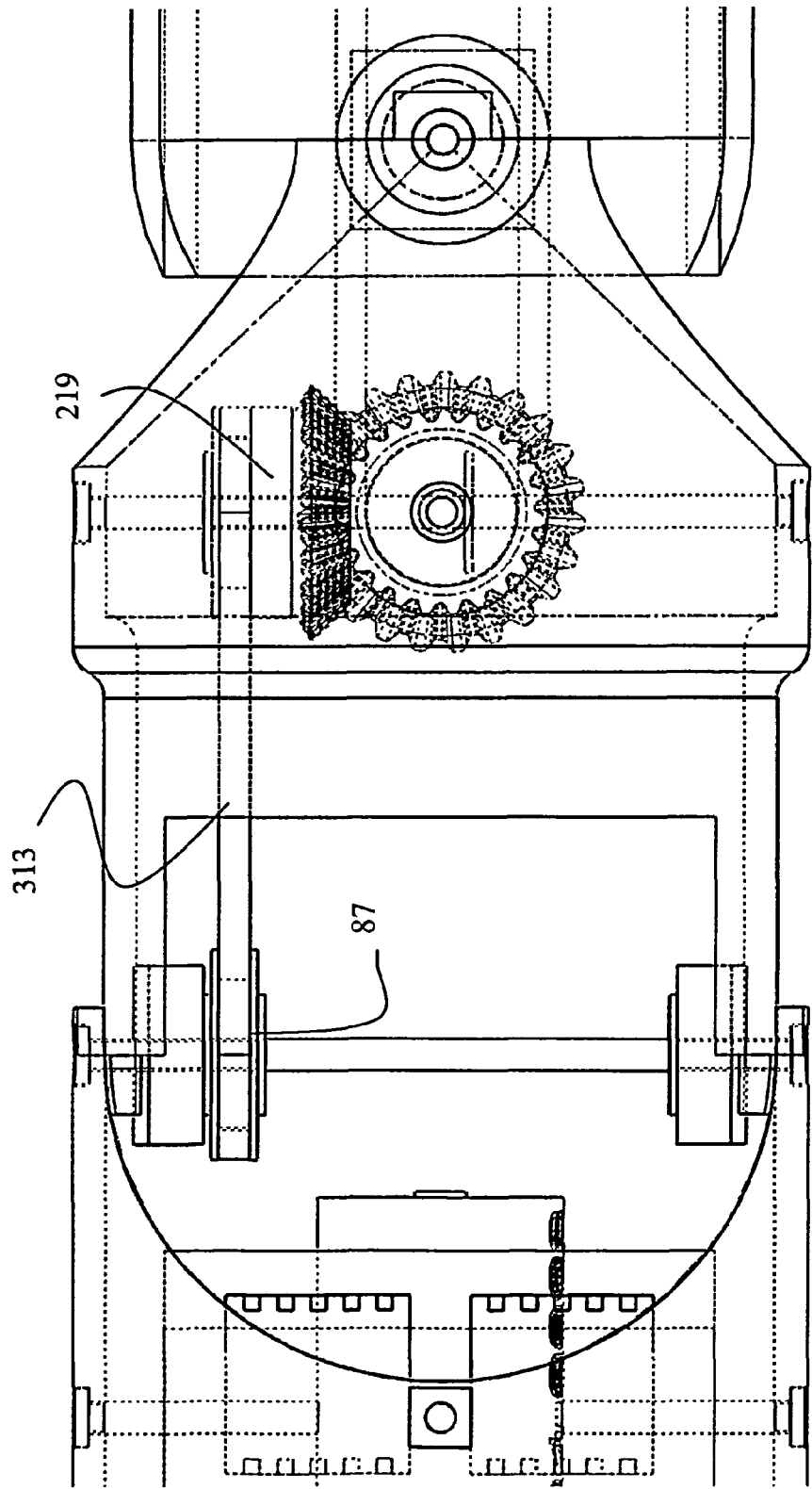
FIG. 37 is a CAD rendering of the cable-drive transmission system in link 4 as viewed from left side plane with hidden lines.

Referring to FIG. 34 and FIG. 37, the transmission system continues through link 4. There, cable 311 rotates fixed pulley 73 which causes rotation of link 3, and thus actuation of pitch DOF4. Then, cable 310 rotates free pulley 217, which in turn rotates another cable 312. This cable rotates the bevel gear and free pulley combination 218 which in turn rotates another bevel gear and free pulley combination 219 while changing the axis of rotation by 90°. The free pulley attached to the bevel gear in 219 then rotates another cable 313. Finally, this cable rotates fixed pulley 87 which causes rotation of link 4, and thus actuation of yaw DOF5. This concludes the remote cable-drive transmission system.

The features of the present invention are summarized as follows:

1. The robotic module consists of a miniature in-vivo manipulator to be used for conducting dexterous manipulations on organs or other entities in a patient's abdominal or peritoneal cavity as part of Natural Orifice Transluminal Endoscopic Surgery.

2. The robotic module is a serial manipulator with seven cylindrical links and six controllable rotational degrees of freedom, thereby enabling an end effector equipped with a laparoscopic instrument to assume a commanded position and orientation within the robot's workspace. Sufficient forces on tissue are provided as geared motors and rigid links are integrated in the device without having to rely on flexible instrumentation.

3. The robotic module is sent from a natural orifice or preexisting wound, possibly through regions such as the esophagus and stomach, and finally into the abdominal cavity via overtube insertion. Once near the target location, the module may be anchored to the inner abdominal skin wall and then guided to the precise desired location via a magnetic anchoring and guidance system. With this, magnetic coupling forces are generated between magnets embedded in the robot and others that are fixed to a different rigid and precise robotic manipulator located external to the patient.

4. The robotic module is wirelessly teleoperated, where commands from a remote (with respect to the patient) computer are transmitted to on-board electronics embedded in the device.

5. The robotic module integrates common commercial-off-the-shelf components such as microcontrollers, wireless transceivers, chip antennas, geared micro-motors with encoders, printed circuit boards, lithium-ion polymer batteries, and permanent magnets. Specific use components depend on the surgical task considered and include different sensor suites and laparoscopic tools such as atraumatic graspers for the end effector.

6. The robotic module constitutes a clinically acceptable device for meeting FDA standards and sterilization requirements because of the use of an outer protective and flexible sheath. The outer diameter is 12 mm which is a significant improvement over similar devices, and the module can be fold up to assume compact configurations. Moreover, a cylindrical geometry for the links minimizes the presence of sharp edges and thus inadvertent damage of tissues.

7. The robotic module contains a cable-drive transmission system for remote actuation instead of direct-drive actuation. This minimizes the overall weight of the module such that the force and torque requirements on the coupling magnets and micro-motors are reduced. It also enables a shorter and more compact module with greater clinical utility. Furthermore, it allows for the use of fewer on-board electronic components and decreased power consumption. The cable-drive transmission system consists of a network of gears, pulleys, and cables and is used to actuate four of the six degrees of freedom.

One skilled in the art will understand that the embodiment of the present invention as shown in the drawings and discussed above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A robotic module for a Natural Orifice Transluminal Endoscopic Surgery (NOTES), comprising: (a) a serial manipulator with seven links and an end effector fitted with a laparoscopic instrument; and (b) a set of protective sheath sections that cover said serial manipulator and that provide a sterilized interface with an in-vivo environment as necessary for clinical applicability, wherein said seven links are arranged to accomplish six controllable rotational degrees of freedom, one passive rotational degree of freedom, two translational degrees of freedom, and additional degrees of freedom according to the type of laparoscopic instrument installed to the end effector, wherein said robotic module is capable of navigating an endoscope type overtube starting from a natural orifice or preexisting wound, through regions of one the esophagus and stomach, and finally into the abdominal or peritoneal cavity, wherein once the said robotic module is placed in a patient's abdominal or peritoneal cavity, said robotic module is anchored to the inner skin wall and guided to a designated location via magnetic coupling forces, wherein when said robotic module is placed at a designated location, said end effector is arranged to follow specified trajectories for arriving at a desired position and orientation within its workspace, wherein said robotic module's end effector and laparoscopic instrument, as well as elements which are one of batteries and sensors are either managed or controlled based on a combination of embedded processing and wireless teleoperation, wherein a team of the said robotic modules may be formed in the abdominal or peritoneal cavity, with each individual robotic module incorporating a set of common elements which are one of on-board electronics, micro-motors, batteries, and magnets, along with specific use elements that may differ among the robotic modules, and which pertain to a desired sensor suite, laparoscopic instrument for the end effector, and any specialized electronics, wherein each of said seven links comprises a rigid structure for maximizing a magnitude of forces imposed by said end effector, and has a cylindrical shape that limits a presence of sharp edges while maintaining a 12 mm outer diameter, thereby facilitating overtube insertion and operation in a delicate in-vivo environment, wherein said first link comprises a magnetic docking interface, a plurality of lithium ion polymer batteries, part of a torsion spring damper mechanism, and on-board electronics consisting of a circular printed circuit board with a microcontroller, a wireless transceiver, and a plurality of motor drivers, and another circular printed circuit board with a compact chip antenna, wherein said second link comprises another magnetic docking interface, part of a torsion spring damper mechanism, a transmission selection servo-motor combination consisting of a geared DC micro-motor with an encoder, a transmission actuation servo-motor combination consisting of a geared DC micro-motor with an encoder, joint dampers, and a portion of a remote cable-drive transmission system consisting of a transmission selection mechanism, a plurality of pulleys, shafts, cables, and gears.

2. The robotic module, as recited in claim 1, wherein said third link comprises a plurality of joint dampers and a portion of a remote cable-drive transmission system consisting of a plurality of several pulleys, shafts, and cables, wherein said fourth link comprises joint dampers and a portion of a remote cable-drive transmission system consisting of a plurality of several pulleys, shafts, and cables.

3. The robotic module, as recited in claim 2, wherein said fifth link comprises joint dampers and a portion of a remote cable-drive transmission system consisting of a plurality of pulleys, bevel gears, shafts, and cables.

4. The robotic module, as recited in claim 3, wherein said sixth link comprises a geared DC micro-motor with embedded sensor feedback, a ball bearing track, a portion of a remote cable-drive transmission system consisting of a pulley, shaft, and cable, and on-board electronics consisting of a rectangular PCB with a microcontroller, wireless transceiver, and motor drivers, and another rectangular PCB with a compact chip antenna.

5. The robotic module, as recited in claim 4, wherein said seventh link comprises a geared DC micro-motor with embedded sensor feedback, lithium ion polymer batteries, a ball bearing track, and elements which are one of shafts and bevel gears for connecting a laparoscopic instrument to the end effector.

6. The robotic module, as recited in claim 5, wherein said torsion spring damper mechanism comprises a spring connected to said first and said second link for generating a restoring force that favors said first and said second link to be parallel to one another, and a damping element which damps oscillations that occur from the spring.

7. The robotic module, as recited in claim 6, wherein said magnetic anchoring and guidance system comprises a magnetic docking interface that works in the following manner: (i) two sets of internal permanent magnets are included in the first and second links for realizing the two said magnetic docking interfaces; (ii) two sets of external permanent magnets located outside of the in-vivo environment (i.e. external with respect to the patient) are placed directly above the patient's abdomen; and (iii) magnetic coupling forces are generated between the said internal and external permanent magnets that act through the abdominal wall thickness.

8. The robotic module, as recited in claim 7, wherein in said magnetic anchoring and guidance system, said external magnets are connected to the end effector of a positioning manipulator for precise motion control.

9. The robotic module, as recited in claim 8, wherein said joint dampers in each of said links are arranged to prevent rotations at joints that are not currently being actuated, but which may otherwise occur from the gravitational force/moment and also due to the coupled nature of the system when other joints are being actuated.

10. The robotic module, as recited in claim 9, wherein said remote cable-drive transmission system works in such a manner that: (i) the transmission selection servo-motor combination in the second link rotates a slider-crank mechanism for translating two sliding gears about a linear track; (ii) the transmission actuation servo-motor combination in the second link rotates the said sliding gears; (iii) a set of four transmission gears in the second link are able to rotate about a shaft and are associated with four transmissions; (iv) the said sliding gears may mesh with only one of the said transmission gears at any given time; (v) the first transmission actuates the joint connecting the second and third links based on a pulley and a cable; (vi) the second transmission remotely actuates the joint connecting the third and fourth links based on a network of pulleys and cables; (vii) the third transmission remotely actuates the joint connecting the fourth and fifth links based on a network of pulleys and cables; and (viii) the fourth transmission remotely actuates the joint connecting the fifth and sixth links based on a network of pulleys, cables, and bevel gears.

11. The robotic module, as recited in claim 10, wherein only four micro-motors for actuation of the joints are utilized, so that said micro-motors are arranged to minimize an overall weight of the module such that the force and torque requirements on the magnets and micro-motors are reduced, a shorter and more compact module with greater clinical utility is possible, and fewer on-board electronics and micro-motors are required which also results in decreased power consumption.

12. The robotic module, as recited in claim 11, wherein said laparoscopic instrument comprises a straight single-action grasping forceps with triangular teeth that includes a non-invasive infrared (IR) temperature sensor installed in an upper blade for constructing an image that depicts the temperature of surrounding tissue and organs.

13. The robotic module, as recited in claim 12, wherein by adopting a roll-pitch-yaw (RPY) convention with the yaw axis defined normal to the inner skin wall, said controllable rotational degrees of freedom are specified as follows: (c1) yaw rotation of the entire robotic module as controlled by the magnetic anchoring and guidance system; (c2) pitch rotation at the second joint (located between the second and third links) as controlled by the first transmission; (c3) pitch rotation at the third joint (located between the third and fourth links) as controlled by the second transmission; (c4) pitch rotation at the fourth joint (located between the fourth and fifth links) as controlled by the third transmission; (c5) yaw rotation at the fifth joint (located between the fifth and sixth links) as controlled by the fourth transmission; and (c6) roll rotation at the sixth joint (located between the sixth and seventh links) as controlled by the geared DC micro-motor installed in the sixth link, wherein the said passive degree of freedom consists of yaw rotation at the first joint (located between the first and second links) that is allowed during module overtube insertion but is constrained by the magnetic coupling that is present during anchoring to the inner abdominal skin wall, wherein the said two translational degrees of freedom of the entire robotic module are provided by the magnetic anchoring and guidance system, and wherein the said additional degree of freedom may be considered as part of the opening and closing motion of the laparoscopic straight single-action grasping forceps.

14. The robotic module, as recited in claim 12, having ranges of motion (ROM) that are sufficient for enabling the robotic module to fold up and assume compact configurations that maximize clinical potential, wherein the second, third, fourth, and fifth joints have ROMs of plus-or-minus 90 degrees, and wherein said first and said sixth joints have ROMs of plus-or-minus 180 degrees.

15. The robotic module, as recited in claim 13, having ranges of motion (ROM) that are sufficient for enabling the robotic module to fold up and assume compact configurations that maximize clinical potential, wherein the second, third, fourth, and fifth joints have ROMs of plus-or-minus 90 degrees, and wherein said first and said sixth joints have ROMs of plus-or-minus 180 degrees.

16. The robotic module, as recited in claim 14, wherein the said embedded processing is accomplished by: (i) on-board electronics in the first link to specifically manage the transmission selection servo-motor combination and transmission actuation servo-motor combination in the second link, as well as the lithium ion polymer batteries at the first link; and (ii) on-board electronics in the sixth link to specifically manage the geared DC micro-motors in the sixth and seventh links, lithium ion polymer batteries in the seventh link, and the infrared sensor installed in the laparoscopic instrument, wherein said wireless teleoperation is enabled by having commands and data sent wirelessly between a remote computer and the robotic module.

17. The robotic module, as recited in claim 15, wherein the said embedded processing is accomplished by: (i) on-board electronics in the first link to specifically manage the transmission selection servo-motor combination and transmission actuation servo-motor combination in the second link, as well as the lithium ion polymer batteries at the first link; and (ii) on-board electronics in the sixth link to specifically manage the geared DC micro-motors in the sixth and seventh links, lithium ion polymer batteries in the seventh link, and the infrared sensor installed in the laparoscopic instrument, wherein said wireless teleoperation is enabled by having commands and data sent wirelessly between a remote computer and the robotic module.

* * * * *